(12) United States Patent
Jones et al.

(10) Patent No.: US 9,321,841 B2
(45) Date of Patent: Apr. 26, 2016

(54) HUMANISED ANTI-CD52 ANTIBODIES

(75) Inventors: Timothy David Jones, Cambridge (GB); Robert George Edward Holgate, Royston (GB); Francis Joseph Carr, Balmedie (GB)

(73) Assignee: ANTITOPE LIMITED, Cambridgeshire (GB)

( * ) Notice: Subject to any disclaimer, the term of this patent is extended or adjusted under 35 U.S.C. 154(b) by 307 days.

(21) Appl. No.: 14/123,349

(22) PCT Filed: Jun. 1, 2012

(86) PCT No.: PCT/EP2012/060345
§ 371 (c)(1),
(2), (4) Date: Jan. 14, 2014

(87) PCT Pub. No.: WO2012/164063
PCT Pub. Date: Dec. 6, 2012

(65) Prior Publication Data
US 2014/0127236 A1 May 8, 2014

Related U.S. Application Data

(60) Provisional application No. 61/492,005, filed on Jun. 1, 2011.

(30) Foreign Application Priority Data

Jun. 1, 2011 (GB) .................................. 1109238.4

(51) Int. Cl.
*A61K 39/395* (2006.01)
*C07K 16/28* (2006.01)
*C12N 15/13* (2006.01)
*A61K 45/06* (2006.01)
*G01N 33/569* (2006.01)
*A61K 48/00* (2006.01)
*A61K 39/00* (2006.01)

(52) U.S. Cl.
CPC ....... *C07K 16/2893* (2013.01); *A61K 39/39541* (2013.01); *A61K 45/06* (2013.01); *G01N 33/56972* (2013.01); *A61K 48/005* (2013.01); *A61K 2039/505* (2013.01); *A61K 2039/57* (2013.01); *C07K 2317/24* (2013.01); *C07K 2317/34* (2013.01); *C07K 2317/55* (2013.01); *C07K 2317/565* (2013.01); *C07K 2317/622* (2013.01); *C07K 2317/73* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| | | |
|---|---|---|
| 7,264,806 B2 | 9/2007 | Carr et al. |
| 7,910,104 B2 | 3/2011 | Carr et al. |
| 2005/0152898 A1 | 7/2005 | Carr et al. |
| 2008/0075715 A1 | 3/2008 | Carr et al. |
| 2008/0248529 A1 | 10/2008 | Carr et al. |
| 2012/0100152 A1 | 4/2012 | Roberts et al. |

FOREIGN PATENT DOCUMENTS

| | | |
|---|---|---|
| CN | 1508155 | 6/2004 |
| WO | 2005/042581 | 5/2005 |
| WO | 2010/132659 | 11/2010 |

OTHER PUBLICATIONS

Fellows, Int'l Search Report for PCT/EP2012/060345, four pages, dated Aug. 31, 2012.

*Primary Examiner* — Phillip Gambel
(74) *Attorney, Agent, or Firm* — Nixon & Vanderhye PC

(57) ABSTRACT

The present invention relates to novel humanised antibodies against human CD52 and their use in methods of treating or preventing human diseases.

21 Claims, 16 Drawing Sheets

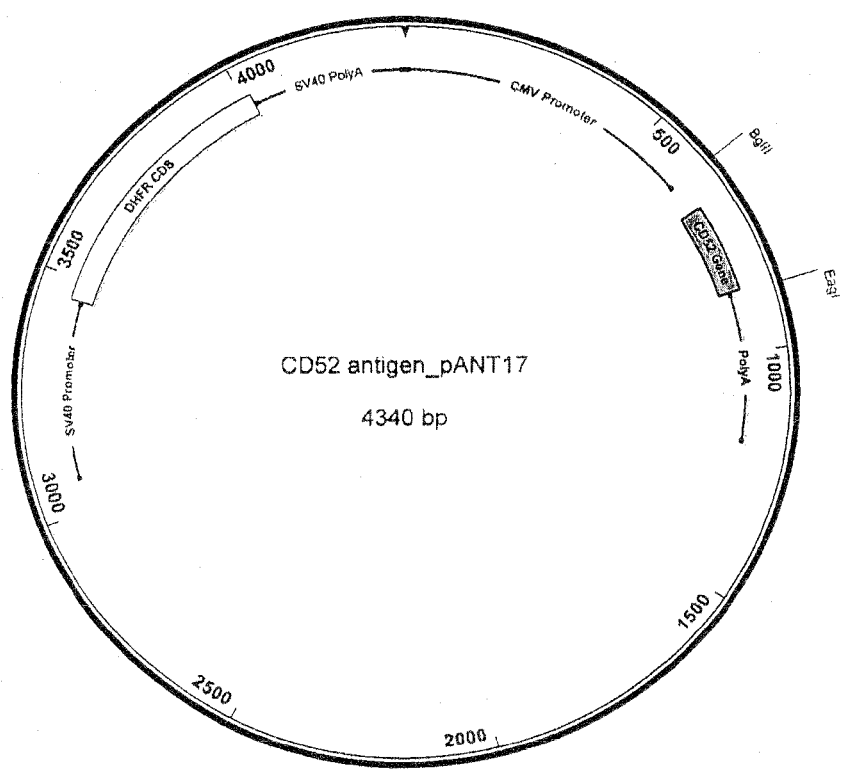
Figure 1a: Human CD52 expression vector

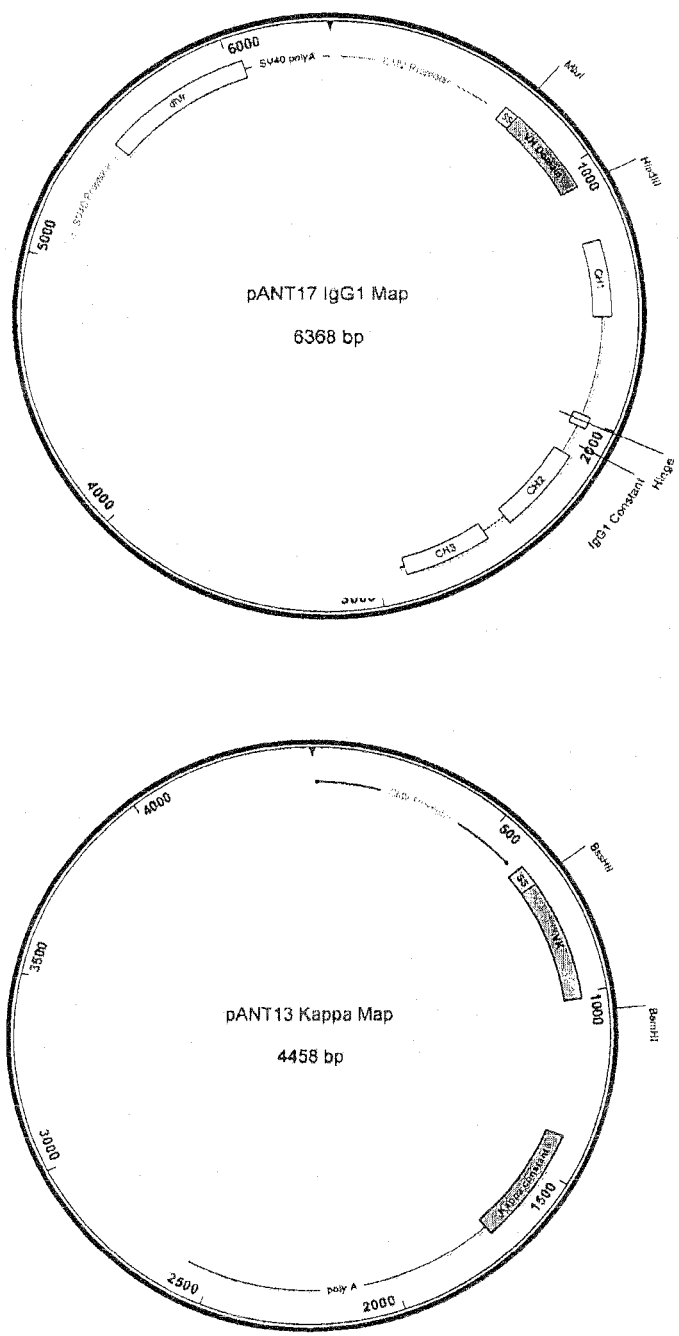
Figure 1b: Human IgG1 / kappa expression vectors (-) F(ab')2 fragment (+) F(ab')2 fragment

HUMANISED ANTI-CD52 ANTIBODIES

This is the national stage of application No. PCT/EP2012/060345, filed Jun. 1, 2012; which claims priority benefit of GB 1109238.4, filed Jun. 1, 2011, and U.S Ser. No. 61/492,005, filed Jun. 1, 2011; the entire contents of each of which are hereby incorporated by reference.

The present invention relates to novel humanised antibodies against human CD52 and their use in methods of treating or preventing human diseases.

BACKGROUND OF THE INVENTION

CD52 is a glycosylated, glycosylphosphatidylinositol (GPI)-anchored cell surface protein found in abundance on a variety of normal and malignant lymphoid cells especially B and T cells (Gilleece et al, Blood 82 807-812 (1993); Hale et al, J Biol Regul Homeost Agents, 15 p386-391 (2001); Rodig et al, Clin Cancer Res 12, p7174-7179 (2006)). CD52 is expressed at lower levels on myeloid cells such as monocytes, macrophages and dendritic cells (DC) with little expression found on mature natural killer (NK) cells, neutrophils, and hematological stem cells. CD52 is also produced by epithelial cells in the epididymis and duct deferens, and is acquired by sperm during passage through the genital tract (Hale et al, ibid,; Domagala et al, Med Sci Monit 7 p325-331 (2001)). The exact biological function of CD52 remains unclear but some evidence suggests that it may be involved in T cell migration and co-stimulation (Masuyama et al, J Exp Med 189 979-989 (1999); Watanabe et al, Clin Immunol 120 247-259 (2006)).

Campath-1H (alemtuzumab, Campath®, MabCampath®) is a humanised anti-human CD52 monoclonal antibody that exhibits potent in vitro antibody-dependent cell mediated cytotoxicity (ADCC) and complement-dependent cytotoxicity (CDC). CD52 is present on at least 95% of all human peripheral blood lymphocytes and monocytes/macrophages (Hale G. et al., The CAMPATH-1 antigen (CD52). Tissue Antigens 1990, 35:118-127). Campath-1H recognizes an epitope which consists of the carboxy terminal four amino acids of the mature CD52 protein and a portion of the negatively charged GPI anchor. Due to its significant cytotoxic effects, Campath-1H is capable of depleting CD52 positive cells in vivo and it is approved for front line and third line treatment of chronic lymphocytic leukemia (CLL). Campath-1H has been evaluated for its utility in the treatment of several autoimmune diseases, including rheumatoid arthritis, vasculitis, myositis, Wegener's disease and diabetes. The most advanced studies of Campath-1H are in treating relapsing remitting multiple sclerosis (MS). These studies showed a significant improvement in time to relapse compared to human interferon beta-1a (Rebif® (i e, interferon beta-Ia)).

A major limitation of Campath-1H is immunogenicity whereby antibodies are induced in up to 70% of patients (Therapeutic Monoclonal Antibodies: From Bench to Clinic, ed. Zhiqiang An (2009) ISBN: 978-0-470-11791-0). In order to improve the clinical utility of anti-CD52 antibodies, there is a major need for improved anti-CD52 antibodies which are not associated with significant immunogenicity in patients.

SUMMARY OF THE INVENTION

The invention relates to humanized immunoglobulins that have binding specificity for human CD52 (huCD52). The invention also provides humanised antibodies that bind to human CD52 with an equilibrium dissociation constant (Kd) of at least $10^{-8}$M. The invention also provides humanised antibodies that specifically bind to human CD52 having an antibody heavy chain of either IgG1, IgG2, IgG3 or IgG4, or using a mutated IgG constant region especially a constant region which enhances ADCC (antibody-dependant cellular cytotoxicity) or CDC (complement-dependant cytotoxicity). The invention also provides humanised antibodies wherein the antibody light chain is a kappa light chain. The humanised antibody can be encoded by human IgG heavy chain and human kappa light chain nucleic acids that encode protein sequences in their variable regions as set forth in SEQ ID NO:20 through SEQ ID NO:28.

The present invention also provides humanised antibodies that specifically bind to human CD52 whereby the antibody variable regions have been selected or modified to exclude one or more human CD4+ T cell epitopes. The present invention also provides humanised antibodies that specifically bind to human CD52 whereby the antibody variable regions have been formed primarily by fusing segments of sequences entirely derived from existing human antibody variable region sequences.

The present invention also provides humanised anti-CD52 antibodies of the invention comprising heavy chain CDR1, CDR2, and CDR3 amino acid sequences, "RYGMS" (SEQ ID NO. 5), "MMKTKGGRTYYPDSVKG" (SEQ ID NO. 6) and "DGYY" (SEQ ID NO. 7), respectively, and light chain CDR1, CDR2, and CDR3 amino acid sequences, "KSSQS-LLHSDGKTYLN" (SEQ ID NO. 8), "LVSKLDS" (SEQ ID NO. 9), and "WQGTHLWT" (SEQ ID NO. 10), respectively. The present invention also provides humanised anti-CD52 antibodies of the invention comprising heavy chain variable region amino acid sequences corresponding to SEQ ID NOS: 20 to 24 for the heavy chain and SEQ ID NOS:25 to 28 for the light chain. In a preferred embodiment of the invention, a humanised anti-CD52 antibody of the present invention comprising heavy chain variable region amino acid sequences corresponding to SEQ ID NO:22 for the heavy chain and SEQ ID NO: 28 is provided.

Humanised antibodies of the present invention can be composed of any of the above CDR sequences SEQ ID NO. 5 to SEQ ID NO. 10 and minor variants of these CDR sequences where alterations of one or more amino acids does not significantly reduce binding to human CD52. Humanised antibodies can be created by joining together the CDR sequences with sequences from human variable region frameworks where such framework sequences are derived from single or multiple other human antibody variable region framework sequences. Commonly such human variable region framework sequences will include one or more mutations which contribute to optimal or improved binding of the humanised antibodies to CD52. In a preferred embodiment of the present invention, such human variable region framework sequences in the humanised antibodies are derived entirely from sequences in other human antibody variable regions as described in of EP1844074. These sequences comprise joined segments of sequences from other human antibody variable regions, together with human constant regions. In particular, such humanised antibodies also contain CDR sequences derived entirely from CDR sequences in other human antibody variable regions including joined segments of CDR sequences from other human CDRs together with human constant regions, thus creating humanised antibodies in which the variable region sequences are derived entirely from sequences in other human antibody variable regions together with human constant regions, this creating a "fully human" antibody.

The invention also provides humanised antibodies that specifically bind to human CD52, wherein said humanised antibody is produced by a prokaryotic or eukaryotic cell, especially from a mammalian cell line, especially CHO or NS0 cells. The invention also provides a humanised antibody that specifically binds to human CD52 that is a Fab fragment or a single chain Fv (scFv). The invention also provides multispecific proteins including at least one humanised antibody from the sequences SEQ ID NOS:20 to 24 for the heavy chain and SEQ ID NOS:25 to 28 for the light chain whereby the multispecific protein specifically binds to human CD52 and, additionally, binds or interacts with one or more other molecules. Different antibodies or proteins may be included in each multispecific antibody can be linked to each other either covalently or non-covalently.

The invention provides a pharmaceutical composition comprising a humanised antibody (either as a proteinaceous antibody or a gene encoding the antibody) that specifically binds to human CD52 and a pharmaceutically acceptable carrier. The pharmaceutical composition can further comprise one or more chemotherapeutic agents either linked or unlinked to the humanised antibody.

The invention provides a method for treatment of CLL and other leukemias; several autoimmune diseases including multiple sclerosis, rheumatoid arthritis, vasculitis, myositis, Wegener's disease and diabetes; and organ transplant rejection and graft-vs-host disease, in each case comprising administering to the patient an effective dosage of a humanised antibody (either as a proteinaceous antibody or a gene encoding the antibody) that specifically binds to human CD52, wherein the antibody causes the destruction or apoptosis of CD52+ target cells such as B and T cells. In addition, the invention also provides a method for diagnosis of the above mentioned diseases, for example by administration of humanised antibody attached to a detectable label and determination of binding of the humanised antibody in vivo to provide a basis for detection of CD52+ cells, for example in localised tumour masses or in inflammatory lesions. Alternatively the humanised antibodies of the present invention may be used for in vitro tests for CD52+ cells as a means for detection of disease and also for in vitro tests for antibodies which may bind to the humanised antibodies used therapeutically. Accordingly, such humanised antibodies of the invention can be used as diagnostic or therapeutic agents in vivo and in vitro.

The humanised antibodies of the invention can encompass various antibody isotypes, or mixtures thereof, such as IgG1, IgG2, IgG3, IgG4, IgM, IgA1, IgA2, IgAsec, IgD, IgE or mutated forms of these IgGs such as mutations which enhance binding to Fc receptors (for example, Horton et al., Blood 116 (2010) p3004-3012) or to complement (for example, Natsume et al., Cancer Res 68 (2008) p3863-3872). Typically humanised antibodies include IgG1 heavy chain constant regions and κ light chain constant regions. The humanised antibodies can be full-length (e.g. IgG1/κ antibody) or can include only an antigen-binding portion (e.g., a Fab, F(ab')2, Fv or a scFv fragment).

Some humanised anti-CD52 antibodies of the present invention can be characterised by one or more of the following properties: a) specificity for human CD52 (specifically binding to human CD52); b) a binding affinity to human CD52 with an equilibrium dissociation constant (Kd) of at least $10^{-8}$M.

In another aspect, the invention provides nucleic acid molecules encoding the humanised antibodies, or antigen-binding portions, of the invention. Accordingly, recombinant expression vectors that include the antibody-encoding nucleic acids of the invention, and host cells transfected with such vectors, are also encompassed by the invention, as are methods of making the antibodies of the invention by culturing these host cells.

Anti-human CD52 humanised monoclonal antibodies of the invention, or antigen binding portions thereof (e.g., Fab), can be derivatised or linked to another functional molecule, e.g., another peptide or protein (e.g., a Fab' fragment). For example, an antibody or antigen-binding portion of the humanised antibodies of the invention can be functionally linked (e.g., by chemical coupling, genetic fusion, noncovalent association or otherwise) to one or more other molecular entities. For example, the humanised anti-CD52 antibody, or antigen binding fragment thereof, can be conjugated to a therapeutic moiety, e.g., a cytotoxic drug, an enzymatically active toxin, or a fragment thereof, a radioisotope, a therapeutic nucleic acid, or a small molecule anti-cancer drug. The antibodies of the invention can also be conjugated to cytotoxic pharmaceuticals, e.g., radiolabeled with a cytotoxic agents such as, e.g. 131I, or can be coupled to a ribosome inactivating protein, e.g. pseudomonas exotoxin (PE38 fragment, plant or bacterial toxins such as ricin, the ax-chain of ricin, saporin, pokeweed antiviral protein, diphtheria toxin, or *Pseudomonas* exotoxin A (Kreitman and Pastan (1998) Adv. Drug Delivery Rev. 31:53.).

In another aspect, the present invention provides compositions, e.g., pharmaceutical and diagnostic compositions, comprising a pharmaceutically acceptable carrier and at least one humanised monoclonal antibody of the invention, or an antigen-binding portion thereof, which specifically binds to human CD52. Some compositions may also comprise a combination of the humanised antibodies or antigen-binding portions of the invention. Such compositions may also comprise combinations with one or more other biologically active molecules as separate molecules, for example, a combination of at least one humanised monoclonal antibody of the invention and another biologically active molecule, or may combine combinations with one or more other biologically active molecules in the same molecule, for example as a bispecific or multispecific molecule either as a combination of two or more humanised antibodies of the invention or as a combination with one or more other biologically active molecules.

For in vivo methods, the humanised antibodies, or antigen-binding portions thereof (or a bispecific or multispecific molecule of the invention) can be administered to a human subject suffering from a disease related to CD52+ cells, or to a disease that can be ameliorated or prevented by treatment with the humanised antibodies of the invention.

Humanised monoclonal antibody compositions of the invention also can be administered in combination with other known therapies, e.g., an anti-cancer therapy, a therapy for an autoimmune disease such as rheumatoid arthritis, or a therapy for multiple sclerosis. Accordingly, the invention provides a method for treating cancer or inflammatory diseases in a subject comprising administering a therapeutically effective amount of a pharmaceutical composition of a humanised antibody together with a pharmaceutical carrier to the subject.

In yet another aspect, the present invention provides a method using antibodies of the invention for detecting in vitro or in vivo the presence of human CD52 antigen in a sample, e.g., for diagnosing a human CD52-related disease. In some methods, this is achieved by contacting a sample to be tested, along with a control sample, with a humanised monoclonal antibody of the invention, or an antigen-binding portion thereof (or a bispecific or multispecific molecule), under conditions that allow for formation of a complex between the antibody and human CD52. Complex formation is then detected (e.g., using an ELISA) in the test samples, and any statistically significant increase in the formation of complexes between the test and control samples is indicative the presence of human CD52 antigen in the test sample.

It will be understood by those skilled in the art that the humanised antibodies of the present invention will have additional uses or compositions beyond those described herein, in all cases where the humanised antibody binds to human CD52 antigen whereby such uses and compositions shall be considered to be within the scope of the invention. It will be understood by those skilled in the art that the variable region sequences of the humanised antibodies of the present invention (SEQ ID NO:20 through SEQ ID NO:28) or CDRs of the humanised antibodies of the present invention (SEQ ID NO:5 through SEQ ID NO:10) may be subject to variations which do not significantly change the properties of the humanised antibodies of the present invention whereby such variants shall be considered to be within the scope of the invention. In addition, such variations either within the variable region or CDR sequences of the humanised antibodies should be considered to be within the scope of the present invention where such variations have significant homology to the humanised sequences of the present invention. For example, a variant nucleic acid may be determined to be within the scope of the invention where this includes sequences containing or substantially identical to SEQ ID NO:11 through SEQ ID NO:19 as determined by its ability to hybridise under stringent conditions to a nucleic acid of the present invention. In one embodiment, a nucleic acid sequence can be determined to be within the scope of the invention (e.g., is substantially identical to SEQ ID NO:11 through SEQ ID NO:19) by its ability to hybridise under stringent conditions to a nucleic acid within the scope of the invention (such as SEQ ID NO:11 through SEQ ID NO:19). The term "hybridise" refers to the binding, duplexing, or hybridising of a molecule to a particular nucleotide sequence under stringent hybridisation conditions when that sequence is present in a complex mixture (e.g. total cellular or library DNA or RNA), wherein the particular nucleotide sequence is detected at least at about 10 times background. Stringent hybridisation conditions will be selected, for example, to be 5-10° C. lower than the thermal melting point (Tm) for the specific sequence at a defined ionic strength pH. It will also be understand that humanised antibodies of the present invention may be modified in the heavy chain constant regions in order to enhance ADCC and CDC. For enhancement of ADCC, fucose-depleted forms of the humanized antibodies may be produced by expression of the antibodies in certain mammalian cells including a variant CHO line, Lec13 (Shields et al., J Biol Chem 277 (2002) p26733-26740), a rat hybridoma cell line, YB2/0 (Shinkawa et al., J Biol Chem 278 (2003) p3466-3473), and a FUT8 (a-1,6-fucosyltransferase) knockout CHO cell line (Yamane-Ohnuki et al., Biotechnol Bioeng 87 (2004) p614-622). Alternatively mutations in the heavy chain constant regions may be used to enhance ADCC such as described by Shields et al., J Biol Chem 276 (2001) p6591-6604 and Lazar et al,. Proc Natl Acad Sci USA 2006; 103 (2006) p4005-4010. Alternatively mutations in the heavy chain constant regions may be used to enhance CDC, for example using antibodies of mixed human IgG1/IgG3 isotype (Natsume et al., ibid).

It will be understood by those skilled in the art, from precedent elsewhere especially from clinical studies with Campath-1H (Zhiqiang An, ibid), that antibodies which bind to human CD52 antigen are fundamentally immunogenic in patients, probably due to the inherent cytotoxicity of anti-CD52 antibodies which acts as co-stimulatory signal to CD4+ T cell epitopes from the antibodies, thus resulting in CD4+ T helper cell responses and immunogenicity. It will therefore be understood by those skilled in the art that the antibodies of the present invention are surprisingly devoid of such CD4+ T helper cell responses as determined by in vitro studies with human blood (cf Example 9) and that such anti-CD52 antibodies with low CD4+ T cell responses (<=4% T cell responses in human T cell assays) are novel.

BRIEF DESCRIPTION OF THE DRAWINGS

Within the figure legends, the nomenclature 2E8 or ANT01 is used interchangeably for mouse, chimeric or humanised antibodies derived from the 2E8 mouse monoclonal antibody.

FIG. 1 shows the plasmid vectors used for expression of chimeric and humanised antibodies in mammalian cells comprising pANT17 for heavy chains and pANT13 for light chains.

EXAMPLES

Figure 2:
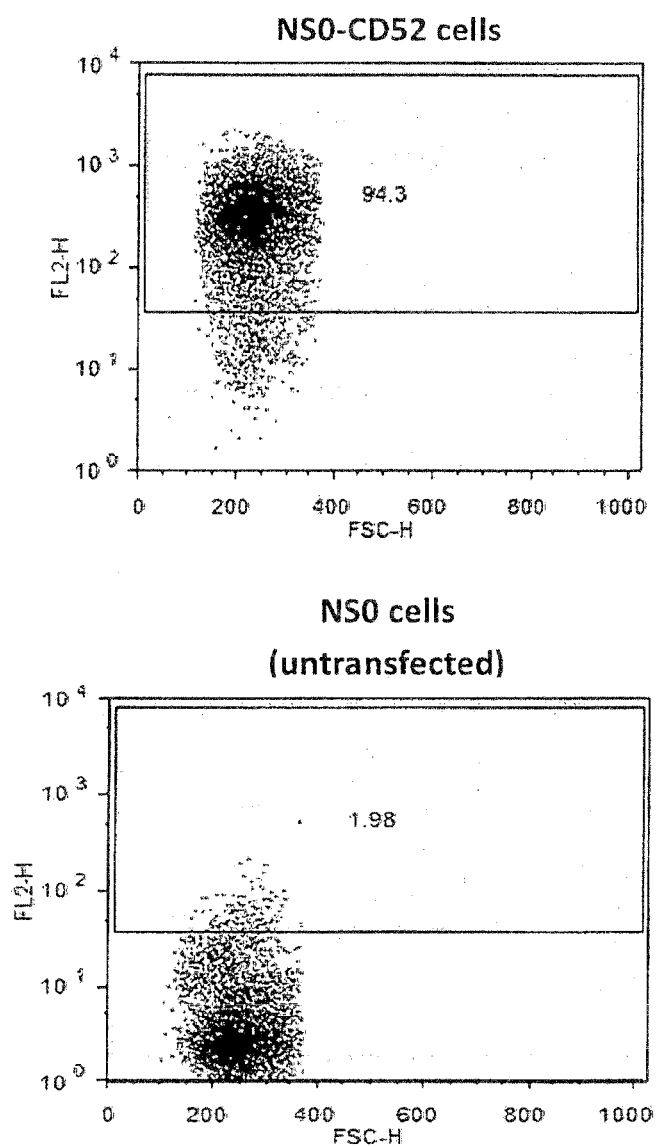
FIG. 2 shows a flow cytometry analysis of binding of the 2E8 mouse monoclonal antibody to NS0 cells transfected with human CD52 compared to binding to NS0 CD52-. Staining was with anti-mouse IgG-PE conjugated antibody with signal derived from PE on the Y axis.

Commercially available reagents referred to in the Examples were used according to manufacturer's instructions unless otherwise indicated. The source of cells identified in the Examples and throughout the specification by ECACC accession numbers is the European Collection of Cell Cultures (ECACC), Salisbury, England. Unless otherwise defined, all technical and scientific terms used herein have the same meaning as commonly understood by one of ordinary skill in the art to which this invention belongs. Exemplary methods and materials are described below although methods and materials similar or equivalent to those described herein can also be used in the practice or testing of the present invention. The materials, methods, and examples are illustrative only and not intended to be limiting in scope.

Example 1

Generation of Mouse Monoclonal Antibodies

CD52 peptide (GQNDTSQTSSPSC) was custom synthesised and conjugated to either KLH or BSA via a maleimidocaproyl-N-Hydroxysuccinimide linker (Mimotopes, Wirral, Cheshire UK) leaving the peptide N-terminus free. Raji and HuT78 cells were obtained from ECACC. CD52-expressing NS0 cell lines were generated as follows: DNA encoding human CD52 (NCBI Reference Sequence: NM_001803.2) (full length sequence including the N-terminal signal peptide, the C-terminal displaced GPI-anchor signal peptide and the mature GPI-anchored surface peptide) was PCR amplified and subcloned into pANT antibody expression vectors (FIG. a) via BglII and EagI sites. Transcription of the CD52 gene was under the control of the CMV I/E promoter (U.S. Pat. Nos. 5,168,062 and 5,385,839, University of Iowa). The pANT expression plasmid contained a mutant dhfr minigene (Simonsen & Levinson 1983, PNAS 80:2495-2499) under the control of a SV40 promoter and polyA sequence for selection in eukaryotic cells as well as a β-lactamase ($Ap^R$) gene for prokaryotic selection and a pMB1 origin of replication for propagation in prokaryotic cells. The expression plasmid was propagated in *E. coli* XL1-blue (Stratagene Cat. No. 200130). Stable CD52 expressing cell lines were obtained by transfecting NS0 cells by electroporation and placing cells under selection with 200 nM methotrexate. Cells were grown and expanded then tested by flow cytometry for CD52 expression. High CD52 expressing cell lines were frozen down and used for immunising mice as described below.

Female Balb/c mice were primary immunised by intraperoneal (i.p.) injection either of 50 ug of CD52 peptide-KLH conjugate in Complete Freund's Adjuvant (CFA), or primary immunised with $1 \times 10^6$ RAJI cells expressing CD52 in phosphate-buffered saline (PBS). After four weeks, all mice were boosted by i.p. injection of $10^6$ HUT-78 cells in PBS with an additional booster injection two weeks later. Four weeks later, all mice received a third boost with $3 \times 10^6$ NS0 cells expressing CD52 in PBS i.p. Two subsequent boosts of $10^7$ NS0 cells expressing CD52 in PBS were injected i.p at two weekly intervals and some mice were given a further boost of 5 ug of CD52 peptide-KLH.

Three days prior to myeloma fusion, the two mice showing the highest antibody titre were given an i.p. boost of $10^7$ NS0 cells expressing CD52 in PBS. On the day of fusion, both mice were sacrificed, spleens were removed, and the cells from each entire spleen were pooled, washed in serum-free culture medium and split into two equal samples. Half of the spleen cells were fused to F0 myeloma cells and half were fused to P3X63Ag8U.1 myeloma cells by PEG-mediated fusion. Plates 1-4 contained the F0 fused cells and plates 5-8 contained the P3X63Ag8U.1 cells. The complete fusion medium consisted of DMEM, 2% L-glutamine, 1% penicillin-streptomycin, 10% fetal bovine serum, 5% BriClone hybridoma cloning medium (National Institute for Cellular Biotechnology, Dublin, Ireland) and Hypoxanthine-Aminopterin-Thymidine (HAT). The resulting fusions were seeded into 96-well plates at 200 ul per well. The remaining non-plated fused cells were stabilized in culture for up to three days, then frozen and stored in liquid nitrogen. The plated fusion cells were cultured at 37° C. in 5% $CO_2$ for two weeks, transferred to 96-well plates, and tested for the presence of secreted anti-CD52 antibodies using the CD52 peptide-KLH ELISA as described below. Cells from 24 immunopositive wells were expanded in culture and tested for CD52-specific antibody by CD52 peptide ELISA, NS0-CD52 cell-based ELISA and by flow cytometry.

For the CD52 peptide ELISA, ELISA plates (VWR, Lutterworth, UK) were coated overnight at 4° C. with 100 ul/well of either CD52 peptide-KLH, CD52 peptide-BSA, KLH only or BSA only at 0.5 µg/ml in PBS. Plates were washed and blocked with 150 ul/well PBS containing 2% BSA. Cell culture supernatants or purified antibodies were diluted in PBS/2% BSA and 100 ul added to each plate followed by incubation for 1 hour at room temperature. Plates were washed three times with PBS-Tween (0.05%) and incubated for 1 hour with 100 ul/well goat anti-mouse Ig (Fab-specific) conjugated to Horseradish Peroxidase (Sigma-Aldrich). Plates were washed three times with PBS-Tween following which SigmaFast OPD substrate (Sigma-Aldrich) was added and incubated at room temperature in the dark to allow colour to develop. The reaction was stopped by adding 50 µl of 3M HCl. Plates were read at 490 nm using a Dynex plate reader (Dynex, Worthing, UK). CD52 peptide-specific hybridomas were those that bound to CD52 peptide-KLH and CD52 peptide-BSA but not to either KLH only or BSA only For the NS0-CD52 cell-based ELISA, $3 \times 10^5$ cells/well (NS0 wild-type or NS0 cells expressing CD52) were plated out in a V-bottom 96 well plate. The plate was centrifuged, supernatants were removed and the plate blotted on absorbent paper. Hybridoma samples were diluted 1 in 2 in FACS buffer (D-PBS containing 1% BSA and 0.05% sodium azide) and 100 µl transferred to each of two plates containing either NS0 (Plate 1) or NS0-CD52 (Plate 2) cells. After incubation at room temperature for 1 hr, the plates were washed twice by centrifuging the plates and resuspending the cells in 200 µl FACS buffer between centrifuging. After centrifugation, cells were resuspended in 100 µl FACS Buffer containing anti-mouse IgG (Fab specific) (Sigma) diluted 1:500. After incubation for 1 hr at room temperature, plates were washed twice by centrifuging and resuspending the cells in PBS. After centrifugation, cells were resuspended in 50 µl PBS and transferred to an ELISA plate. 100 µl TMB substrate (Invitrogen) was added and incubated at room temperature in the dark to allow the colour to develop. The reaction was stopped by adding 50 µl of 3M HCl. Plates were read at 450 nm using Dynex plate reader. CD52-specific clones were those that bound to NS0-CD52 cells specifically when compared with NS0 wild-type cells.

For flow cytometry, $3 \times 10^5$ cells NS0-CD52 or wild-type NS0 were stained using a 1 in 2 dilution of anti-CD52 hybridomas antibodies together with a 1 in 100 dilution of anti-mouse IgG-PE conjugated antibody (Sigma). Mouse IgG (Sigma) was also included as a separate control for the different murine isotypes present within the hybridomas. Cells were stained for 1 hour at 4° C. An anti-mouse IgG-PE conjugated antibody only control was also included. Cells were washed twice with FACS buffer and finally resuspended in FACS buffer and flow cytometry performed using a Beckton Dickinson FACSCalibur (Becton Dickinson, Oxford, UK). Instrument settings were determined by analysis of relevant isotype control antibodies.

From results of CD52 peptide ELISA, NS0-CD52 cell-based ELISA and flow cytometry, huCD52 specific hybridomas were cloned, expanded in culture, frozen as parental stocks and stored in liquid nitrogen. Each of the selected hybridomas was diluted in cloning medium and plated into 96-well plates at a cell density of one cell per three wells. Cloning medium consisted of DMEM, 2% L-glutamine, 1% penicillin-streptomycin, 10% fetal bovine serum, 5% Bri-Clone hybridoma cloning medium and hypoxanthine-thymidine (HT). Cultures were maintained at 37° C. in 5% $CO_2$ for 2 weeks with the cloned cells receiving fresh medium after one week in culture. Two weeks after cloning, supernatants from all seeded wells were transferred to new 96-well plates and tested for the presence of anti-CD52 antibodies using the CD52 peptide ELISA and flow cytometry as described previously. Positive wells were expanded in culture and retested. Positive cells were further expanded and tested for antibody isotype. Anti-CD52 positive subclones were frozen, stored in liquid nitrogen and used for monoclonal antibody production for further studies.

Monoclonal antibodies were isotyped using the Rapid ELISA Mouse Antibody Isotyping Kit (Perbio, Cramlington, UK). Antibodies were purified on a 1 ml Protein A-sepharose column (GE Healthcare, Little Chalfont, UK). Prior to purification, both the tubing and the Protein A column were depyrogenated using 0.4M NaOH. The column was re-equilibrated with 20 column volumes of PBS pH 7.4. Hybridoma cell culture supernatants were harvested, adjusted to 1× PBS pH 7.4 using 10× PBS and filter sterilised. Filtered supernatant was pumped through on the Protein A-sepharose column at 0.5 ml/min. The column was washed with 1x PBS pH 7.4 and IgG was eluted using sterile 0.1M Sodium Citrate pH3, with 0.9 ml fractions collected and neutralised with 0.1 ml of sterile 1M Tris-HCl pH 9. Under sterile conditions, the product was buffer exchanged into PBS pH 7.4 to remove any elution buffer and concentrate the sample. After concentration, antibodies were quantified by OD280 nm using an extinction coefficient, Ec (0.1%) of 1.4. Purified antibodies were analysed by SDS-PAGE using a Novex NuPAGE electrophoresis system with 4-12% NuPage gel (Invitrogen, Paisley, UK) and MES running buffer. 1 μg of antibody was prepared with 4× NuPAGE sample buffer plus beta-mercaptoethanol and heated. The gel was stained with InstantBlue staining solution (Expedeon, Cambridge, UK) and molecular size were estimated by comparing stained bands to PageRuler™ Plus Prestained Protein Ladder (Fermentas, York, UK). Two bands were identified for each antibody with no detectable contamination present. Purified antibodies were testing using the CD52 peptide flow cytometry as described above. From flow cytometry analysis (FIG. 2), the lead monoclonal antibody designated 2E8 was shown to bind selectively to NS0-CD52 cells.

Example 2

Variable Region Gene Sequencing

Total RNA was extracted from 2E8 hybridoma cells using the RNAqueous-4PCR Kit (Ambion, Warrington, UK) and used to synthesis cDNA. Murine immunoglobulin heavy and kappa light chain variable (V) region fragments were amplified by PCR using degenerate mouse leader sequence primers (Sigma) and unique constant domain primers (Sigma) as shown in Table 1. The resulting PCR fragments were subcloned into the pGEM-T Easy I vector system (Promega, Southampton, UK) and inserts were sequenced using the vector-specific primer, M13Forward (Sigma) All DNA sequencing was performed by Geneservice Ltd, Cambridge, UK). The resultant V region nucleotide sequences are shown as SEQ ID No. 1 and SEQ ID No. 2 and corresponding amino acid sequences as SEQ ID No. 3 and SEQ ID No. 4 for heavy and light chain V regions respectively.

TABLE 1

| Sequence | Name-Pool |
| --- | --- |
| ATGRASTTSKGGYTMARCTKGRTTT | $MuIgV_H5'$-A |
| ATGRAATGSASCTGGGTYWTYCTCTT | $MuIgV_H5'$-B |
| ATGGACTCCAGGCTCAATTTAGTTTTCCT | $MuIgV_H5'$-C |
| ATGGCTGTCYTRGBGCTGYTCYTCTG | $MuIgV_H5'$-C |
| ATGGVTTGGSTGTGGAMCTTGCYATTCCT | $MuIgV_H5'$-C |
| ATGAAATGCAGCTGGRTYATSTTCTT | $MuIgV_H5'$-D |
| ATGGRCAGRCTTACWTYYTCATTCCT | $MuIgV_H5'$-D |
| ATGATGGTGTTAAGTCTTCTGTACCT | $MuIgV_H5'$-D |
| ATGGGATGGAGCTRTATCATSYTCTT | $MuIgV_H5'$-E |
| ATGAAGWTGTGGBTRAACTGGRT | $MuIgV_H5'$-E |
| ATGGRATGGASCKKIRTCTTTMTCT | $MuIgV_H5'$-E |
| ATGAACTTYGGGYTSAGMTTGRTTT | $MuIgV_H5'$-F |
| ATGTACTTGGGACTGAGCTGTGTAT | $MuIgV_H5'$-F |
| ATGAGAGTGCTGATTCTTTTGTG | $MuIgV_H5'$-F |
| ATGGATTTTGGGCTGATTTTTTTATTG | $MuIgV_H5'$-F |
| CCAGGGRCCARKGGATARACIGRTGG | $MuIgGV_H3'$-2 |
| ATGRAGWCACAKWCYCAGGTCTTT | $MuIgkV_L5'$-A |
| ATGGAGACAGACACACTCCTGCTAT | $MuIgkV_L5'$-B |
| ATGGAGWCAGACACACTSCTGYTATGGGT | $MuIgkV_L5'$-C |
| ATGAGGRCCCCTGCTCAGWTTYTTGGIWTCTT | $MuIgkV_L5'$-D |
| ATGGGCWTCAAGATGRAGTCACAKWYYCWGG | $MuIgkV_L5'$-D |
| ATGAGTGTGCYCACTCAGGTCCTGGSGTT | $MuIgkV_L5'$-E |
| ATGTGGGGAYCGKTTTYAMMCTTTTCAATTG | $MuIgkV_L5'$-E |
| ATGGAAGCCCCAGCTCAGCTTCTCTTCC | $MuIgkV_L5'$-E |
| ATGAGIMMKTCIMTTCAITTCYTGGG | $MuIgkV_L5'$-F |
| ATGAKGTHCYCIGCTCAGYTYCTIRG | $MuIgkV_L5'$-F |
| ATGGTRTCCWCASCTCAGTTCCTTG | $MuIgkV_L5'$-F |
| ATGTATATATGTTTGTTGTCTATTTCT | $MuIgkV_L5'$-F |
| ATGAAGTTGCCTGTTAGGCTGTTGGTGCT | $MuIgkV_L5'$-G |
| ATGGATTTWCARGTGCAGATTWTCAGCTT | $MuIgkV_L5'$-G |
| ATGGTYCTYATVTCCTTGCTGTTCTGG | $MuIgkV_L5'$-G |
| ATGGTYCTYATVTTRCTGCTGCTATGG | $MuIgkV_L5'$-G |
| ACTGGATGGTGGGAAGATGGA | $MuIgkV_L3'$-1 |

Sequences of the 2E8 hypervariable regions (CDRs) were as follows;

| | | |
|---|---|---|
| CDRH1 | RYGMS | SEQ ID NO. 5 |
| CDRH2 | MMKTKGGRTYYPDSVKG | SEQ ID NO. 6 |
| CDRH3 | DGYY | SEQ ID NO. 7 |
| CDRL1 | KSSQSLLHSDGKTYLN | SEQ ID NO. 8 |
| CDRL2 | LVSKLDS | SEQ ID NO. 9 |
| CDRL3 | WQGTHLWT | SEQ ID NO. 10 |

Example 3

Generation of Chimeric Antibody

The heavy and light chain V region sequences of the 2E8 monoclonal antibody were PCR amplified and subcloned into pANT antibody expression vectors (FIG. 1b) with heavy and light chain V regions cloned into pANT17 and pANT13 respectively. Heavy chain V region genes were cloned into pANT17 via M1uI and HindIII sites in frame with the human γ1 heavy chain gene (G1m3 (G1m(f)) allotype) and light chain V region genes were cloned into pANT13 via BssHII and BamHI sites in frame with the human kappa light chain constant region gene (Km3 allotype). Transcription of both heavy and light chain genes was under the control of the CMV I/E promoter (U.S. Pat. No. 5,168,062 and U.S. Pat. No. 5,385,839, University of Iowa) and the pANT17 plasmid contained a mutant dhfr minigene (Simonsen & Levinson 1983, PNAS 80:2495-2499) under the control of a SV40 promoter and polyA sequence for selection in eukaryotic cells. Both pANT17 and pANT13 contained a β-lactamase (Ap$^R$) gene for prokaryotic selection and a pMB1 origin of replication for propagation in prokaryotic cells. All plasmids were propagated in *E. coli* XL1-blue (Stratagene Cat. No. 200130). Primers used to amplify the variable region genes for cloning into the pANT expression vectors are shown in Table 2.

etry analysis when competed with Campath-1H for binding to CD52+ HuT78 cells.

Example 4

Antibody-Dependent Cell-Mediated Cytotoxicity (ADCC)

Figure 5:
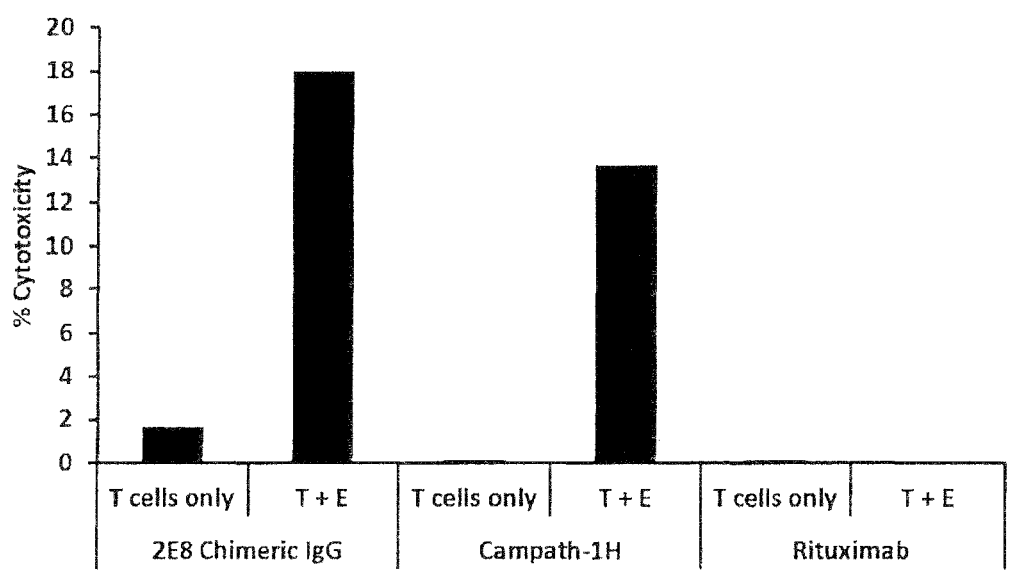
FIG. 5 shows the mean cytotoxicity from 5 human PBMC samples used as effector cells in an ADCC assay for chimeric 2E8 and Campath-1H with REH target cells.
Figure 6:
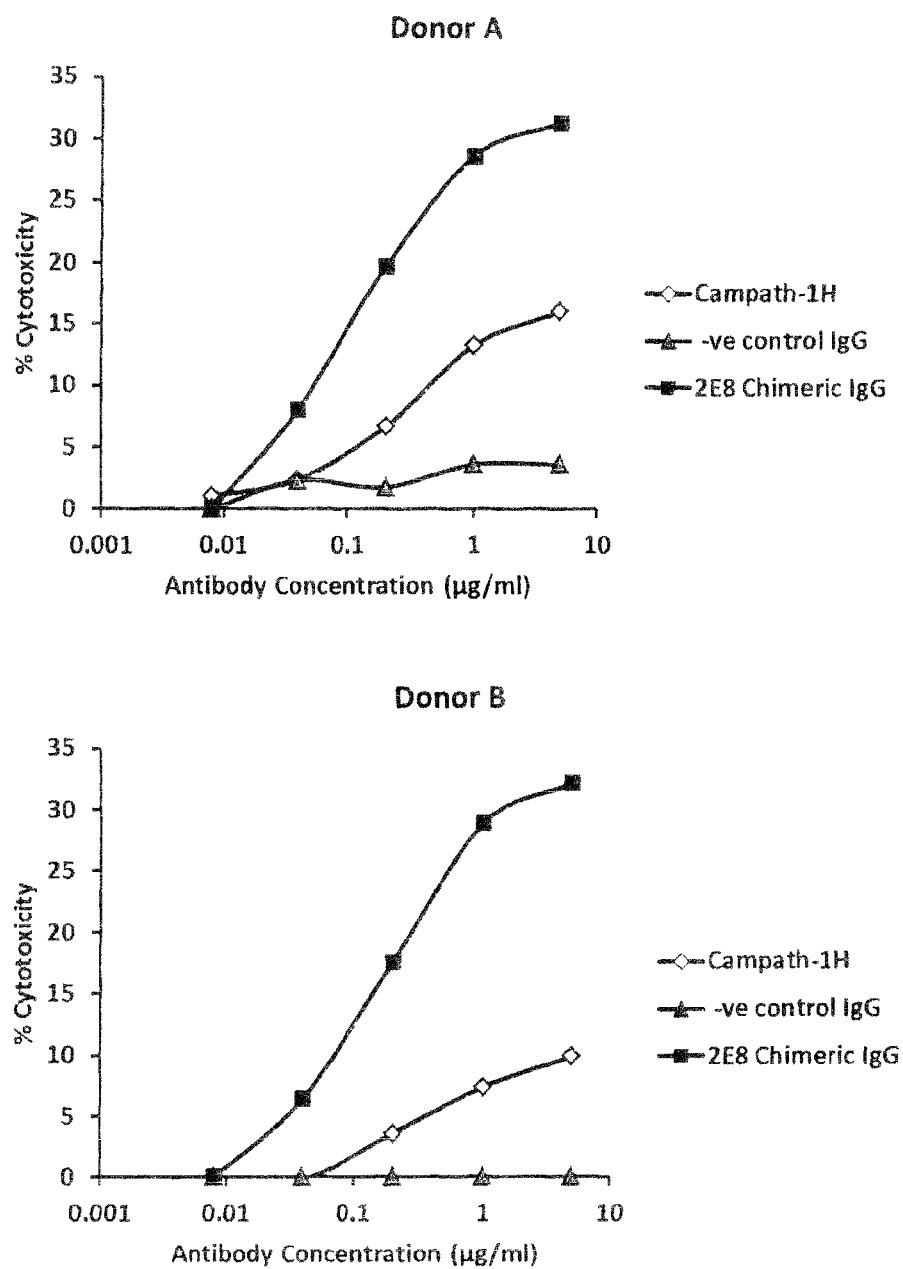
FIG. 6—as FIG. 5 except for 2 individual PBMC with dilutions of chimeric 2E8 and Campath-1H with high expressing REH target cells.

ADCC assays were performed with the 2E8 monoclonal antibody as follows. Target cells (either REH or Raji cells) were harvested and preloaded with 25 μM (final) Calcein-AM (Sigma). After incubation with Calcein for 1 hr at 37° C., cells were washed in media to remove unincorporated Calcein. 1×10$^4$ target cells were added to a clear V-bottomed plate containing 2E8 or control antibodies at 50 μg/ml final as in FIG. 5 or as depicted in FIG. 6, and incubated for 1 hr to pre-opsonise the target cells. PBMCs (effector cells) were isolated from healthy community donor buffy coats (from blood drawn within 24 hours) obtained from the UK National Blood Transfusion Service (Addenbrooke's Hospital, Cambridge, UK) and according to approval granted by Addenbrooke's Hospital Local Research Ethics Committee. PBMCs were isolated from buffy coats by Lymphoprep (Axis-Shield, Dundee, UK) density centrifugation. 5'10$^5$ effector cells were added to each well of the plate containing target cells and antibody in a final volume of 250 μl (50:1 ratio of effector to target cells). Samples were incubated for 4hr at 37° C./5% CO$_2$. After 4 hours, Triton X-100 was added to the control wells containing cells (effector and/or target cells) to establish the maximum lysis control. Following centrifugation, 150 μl media was transferred from each well to a 96 well clear-bottom black-walled plate and the plate fluorescence was measured at 520 nm Results were expressed as:

$$\% \text{ Cytotoxicity} = \frac{(\text{test sample signal minus background Calcein-AM release})}{(\text{maximum target cell lysis signal minus background Calcein-AM release})} \times 100$$

TABLE 2

| Sequence | Name |
|---|---|
| ctgttgctacgcgtgtccactccGAGGTGCACCTGATGGAG | 2E8 VH 5' |
| ctgccccagaaagcttaccTGAGGAGACTGTGAGAGTG | 2E8 VH 3' |
| ggctcccaggcgcgcgatgtGATGTTTTGATGACCCAGAC | 2E8 VK 5' |
| gaattgcgggatccaactgaggaagcaaagtttaaattctactcacgTTTGATTTCCAGTTTGGTGCC | 2E8 VK 3' |

Figure 3:
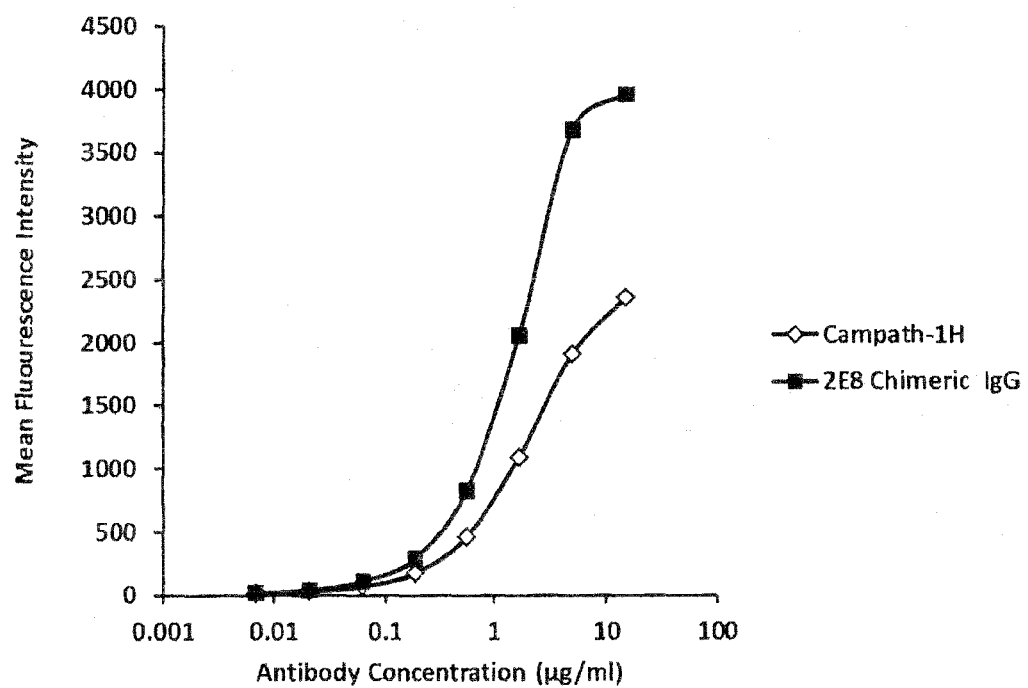
FIG. 3 shows a flow cytometry analysis of binding of dilutions of chimeric 2E8 to Hut78 cells compared to Campath-1H. Staining was with anti-human IgG-PE conjugated antibody.
Figure 4:
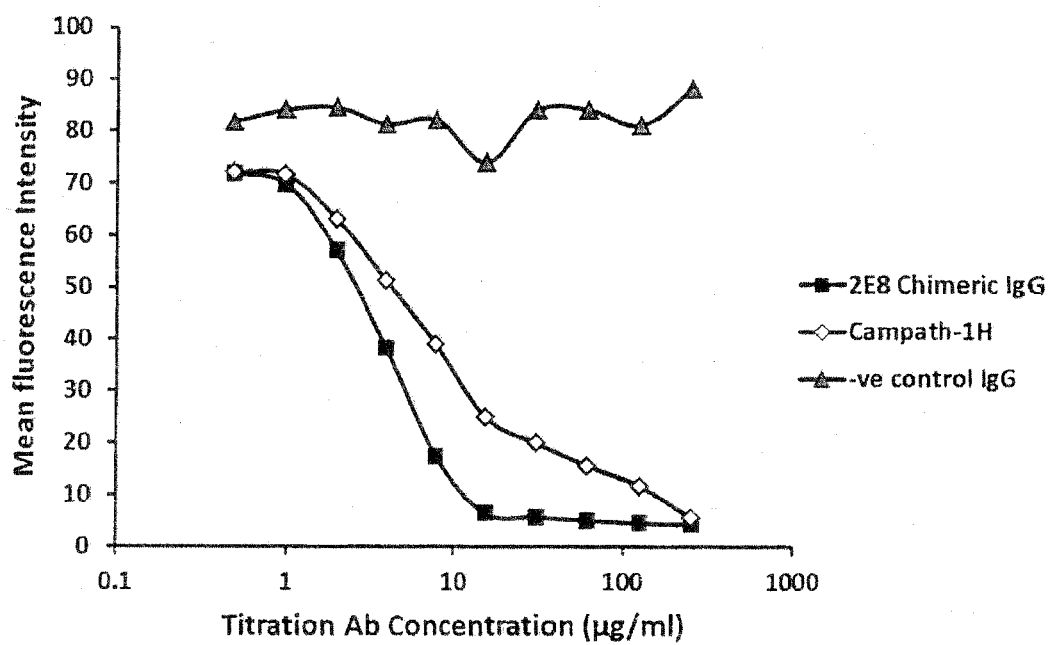
FIG. 4 shows a competition flow cytometry analysis using Campath-1H-PE in competition with chimeric 2E8 and Campath-1H for binding to Hut78 cells.

The heavy and light chain expression constructs were then co-transfected either transiently into HEK293 cells by calcium phosphate-based transfection or stably transfected into NS0 cells by electroporation. Secreted antibody was purified from the cell culture supernatants by Protein A chromatography. As shown in FIG. 3 using flow cytometry analysis as detailed in Example 1, dilutions of the 2E8 antibody exhibited an improved binding profile to CD52+ HuT78 cells compared to Campath-1H. As shown in FIG. 4, the 2E8 antibody exhibited an improved competitive binding profile by flow cytom- FIG. 5 shows the mean ADCC for PBMC from 5 human donors for chimeric 2E8 ('ANT01') and Campath-1H for target CD52+ REH cells showing a significantly enhanced ADCC for chimeric 2E8. Subsequently a high CD52 expressing variant REH cell line was isolated by FACS which exhibited approximately 2× the binding of Campath-1H compared to the parent REH cells. FIG. 6 shows a dilution series of chimeric 2E8 and Campath-1H for ADCC on high CD52+ REH cells using PBMC from two individual donors. This also shows the significantly enhanced ADCC profile for chimeric 2E8 compared to Campath-1H.

Example 5

Complement-Dependent Cytotoxicity (CDC)

Figure 7:
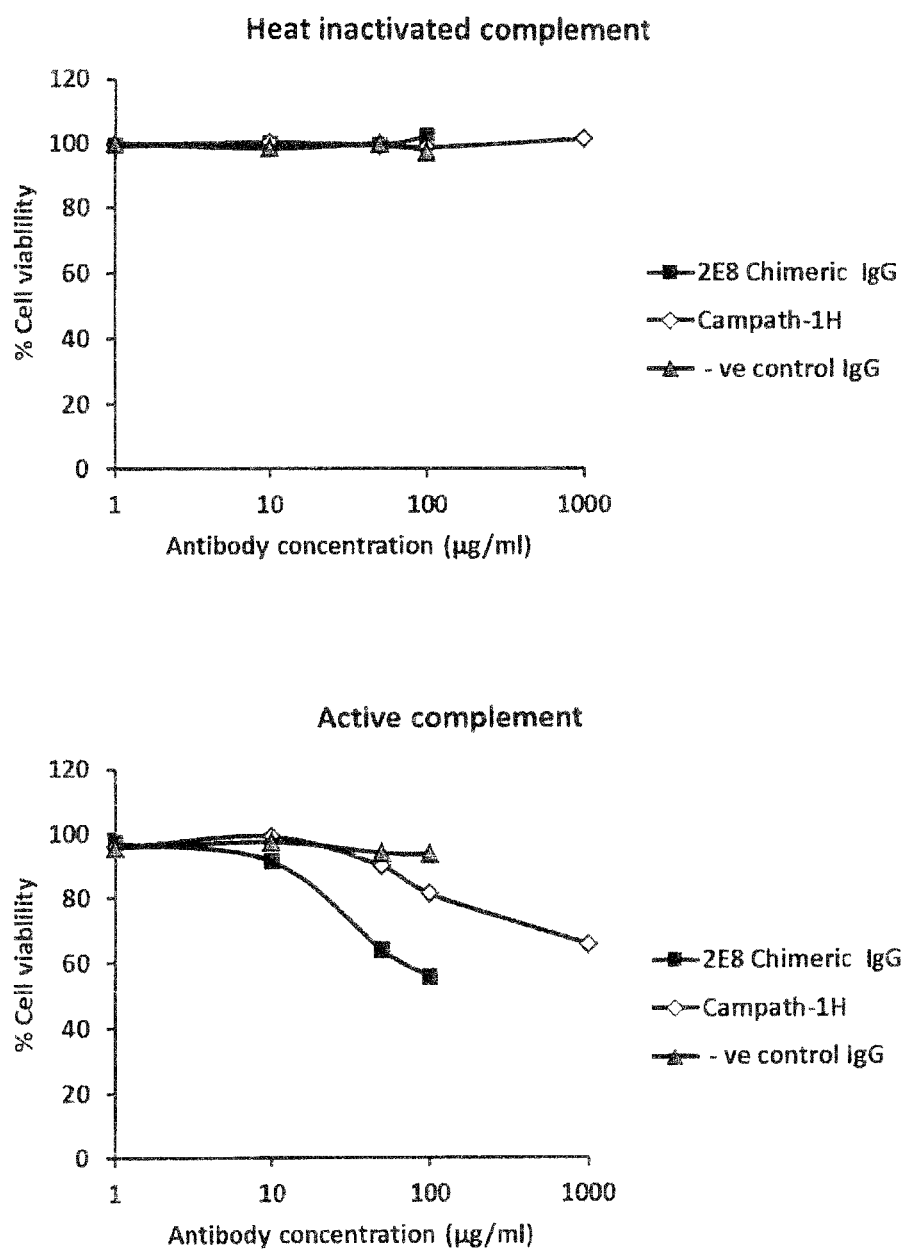
FIG. 7—as FIG. 6 except using human complement for CDC assays with dilutions of chimeric 2E8 and Campath-1H and high expressing REH target cells.

CDC assays were performed on the 2E8 monoclonal antibody as follows. Target cells (either REH or Raji cells) were harvested and 5×10$^4$ cells/well were added to a black-walled, clear flat-bottomed 96 well plate. 2E8 or control antibodies for final concentrations as shown in FIG. 7 were added together with either active or heat inactivated (@60° C. for 30 min) human serum (Pathway Diagnostics Ltd, Dorking, UK) per well (25% final serum concentration). Samples were incubated for 3 hr at 37° C./5% $CO_2$. After 3 hours, Triton X-100 was added to the control cell containing wells to establish the maximum lysis control. Prestoblue (10×) cell viability reagent (Invitrogen) was diluted with assay growth media and added to each well to obtain a final 1 in 10 dilution of Presto-Blue. After incubation for 1 hr at 37° C./5% $CO_2$, the plate fluorescence was measured at 590 nm Results were expressed as:

$$\% \text{ Cell Viability} = \frac{(\text{Sample minus background release})}{(\text{max readout (No lysis) minus background readout})} \times 100$$

FIG. 7 shows a significantly enhanced CDC profile for chimeric 2E8 compared to Campath-1H.

Example 6

Generation of Humanised Antibodies

Humanised antibodies were generated using methods described in EP1844074 (Antitope Ltd). Structural models of the mouse 2E8 V regions were produced using Swiss PDB and analysed in order to identify important amino acids that were likely to be important for the CD52 binding properties of the antibody ('constraining residues'). A database of human V region sequences was used to identify segments of human V region sequences containing each of the constraining residues to be used in design of the humanised antibodies. Typically two or more alternative V region sequence segments were used to provide each constraining residue resulting in a large range of possible sequences of humanised anti-CD52 V region sequences for 2E8. These sequences were then analysed for the prediction of non-germline MHC class II peptide binding by in silico analysis as described in Fothergill et al. (WO9859244, assignee Eclagen Ltd) and also for known CD4+ T-cell epitopes using databases including "The Immune Epitope Database and Analysis Resource", http://www.immuneepitope.org/. V region sequences with predicted non-germline MHC class II binding peptides, or with significant hits against T cell epitope databases were discarded. This resulted in a reduced set of V region sequences. Selected combinations of V region sequence segments were then combined to produce humanised heavy and light chain variable region amino acid sequences. Five heavy chains and four light chain sequences (designated VH1 to VH5, and VK1 to VK4 respectively) were selected for 2E8 (SEQ ID No.s 20 to 24 and 25 to 28 respectively).

DNA encoding humanised variant V regions were synthesised and subcloned into the expression vectors pANT17 and pANT13 (FIG. 1) as described in Example 3. All combinations of humanised VH and VK chains (i.e. a total of 20 pairings for 2E8) were transiently transfected into HEK293 and also transfected into NS0 cells, and antibody was purified by protein A chromatography from the culture supernatants as described in Example 3.

Example 7

Analysis of Humanised Antibodies

The binding of HEK-derived and NS0-derived 2E8 humanised variants to CD52 peptide was assessed in a competition ELISA against the parent chimeric antibody. The parental 2E8 chimeric antibody was biotinylated using Biotin Tag™ Micro Biotinylation kit (Sigma-Aldrich). 96 well MaxiSorp plates (Nunc) were coated with 0.025 µg/ml CD52 peptide-KLH in Dulbecco's PBS (PAA Laboratories, Yeovil, UK) (100 µl final volume) at 4° C. overnight. Plates were blocked with Dulbecco's PBS-2% BSA for 1 hour at room temperature. Plates were washed 3 times with wash buffer (0.05% Tween20 in Dulbecco's-PBS). Test humanised antibodies at various concentrations were premixed with biotinylated parent chimeric antibody (0.035 µg/ml final concentration) and then added to the CD52 peptide-KLH plate (100 µl final volume). All samples were tested in duplicate. Plates were incubated for 1 h at room temperature and washed 3 times with wash buffer. 100 µl of a 1 in 1000 dilution of Streptavidin HRP (Sigma-Aldrich) was added and incubated for 1 hour at room temperature. Plates were washed 3 times with wash buffer and 100 µl of TMB substrate (Invitrogen) was added and incubated at room temperature in the dark to allow the colour to develop. The reaction was stopped by adding 50 µl of 3M HCl. Plates were read at 450 nm using Dynex plate reader.

Figure 8:
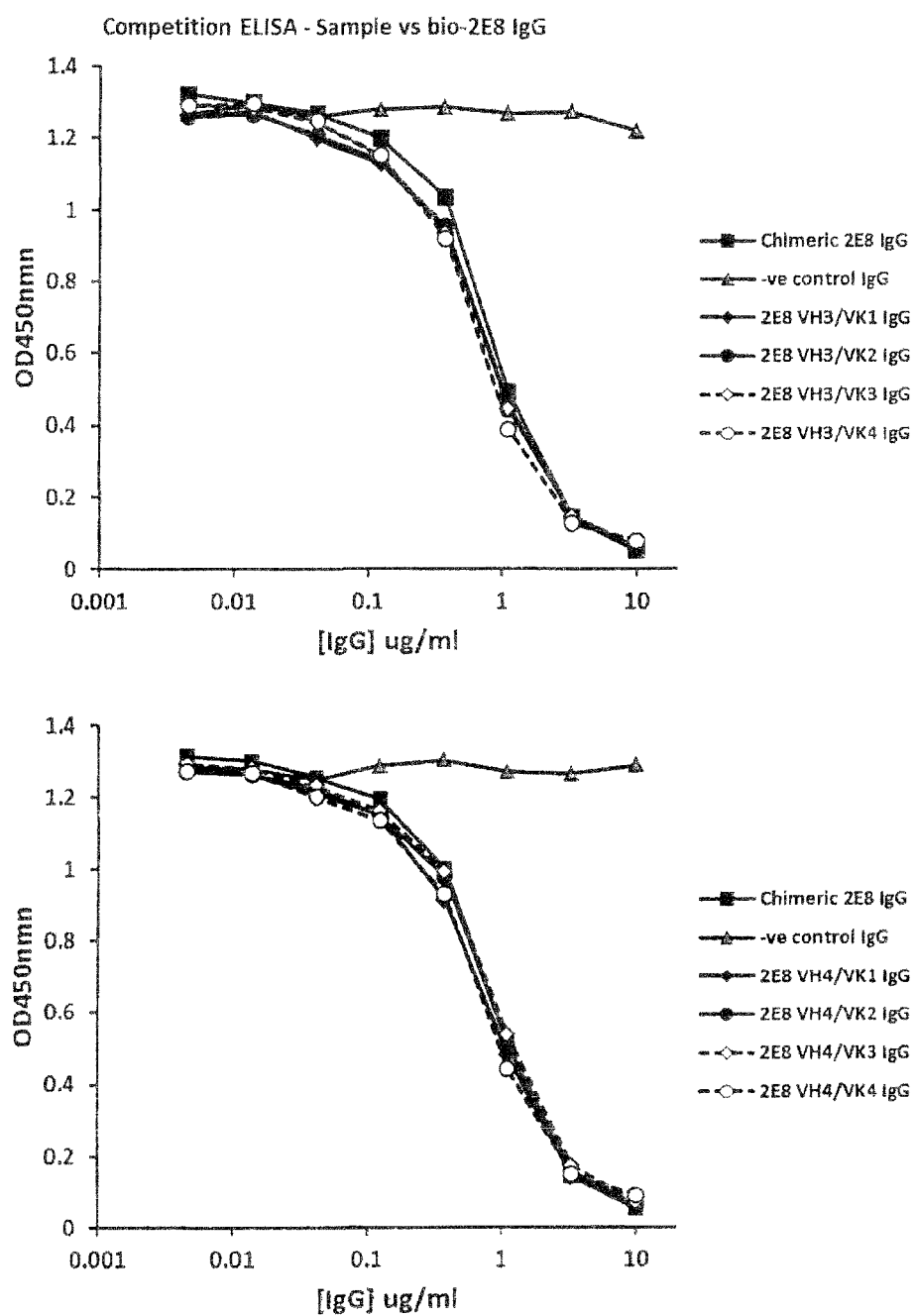
FIG. 8 shows a competition CD52 peptide ELISA for binding of humanised 2E8 variants in competition with biotinylated chimeric 2E8.
Figure 9:
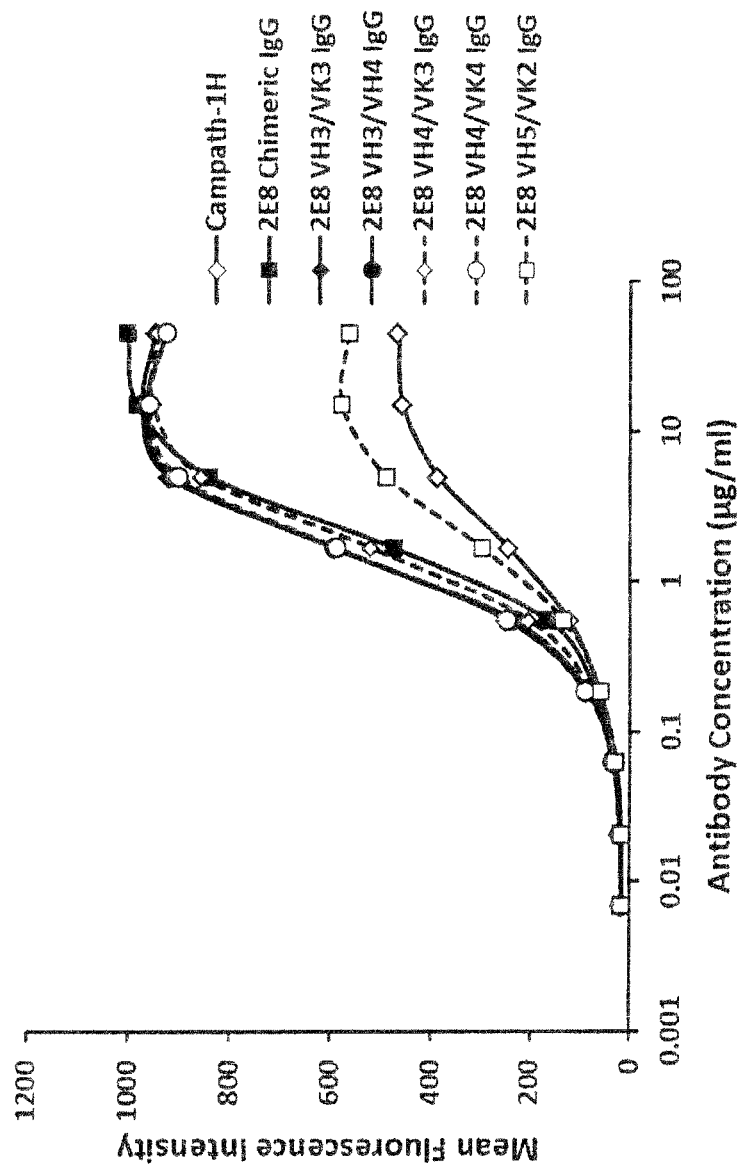
FIG. 9 shows a flow cytometry analysis for binding of dilutions of humanised variants and Campath-1H to REH cells.
Figure 10:
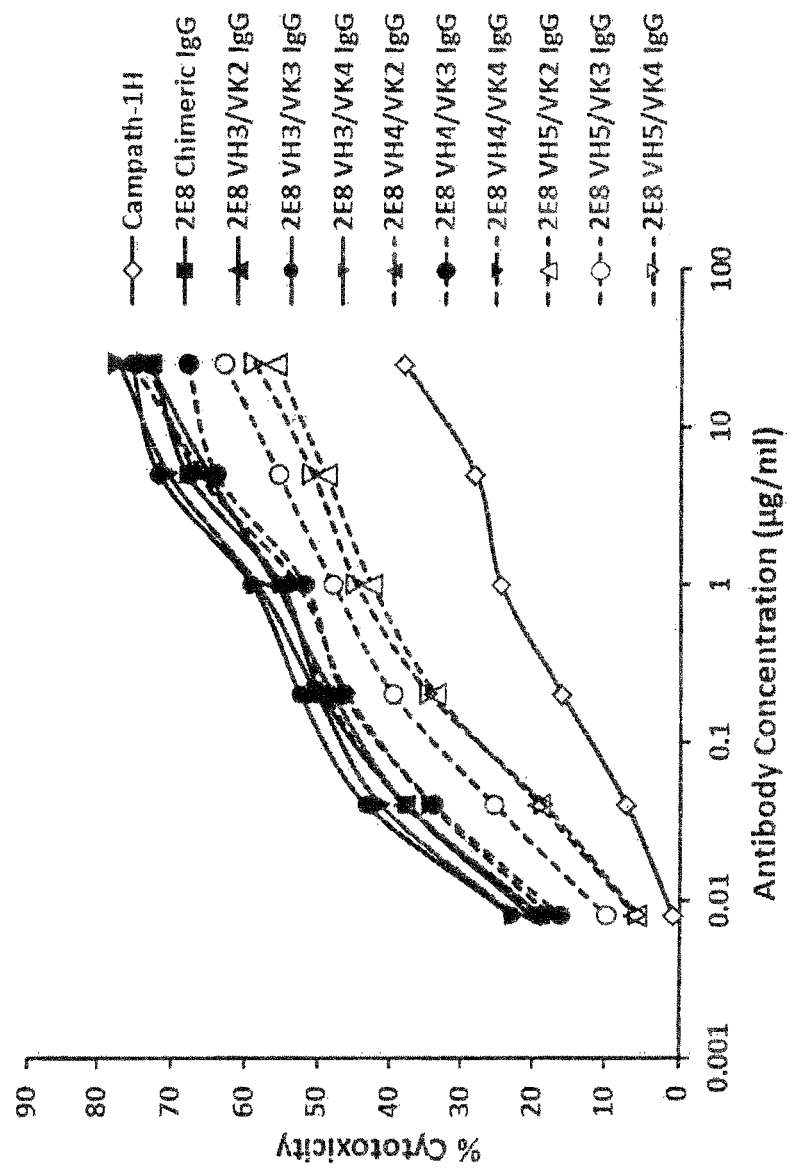
FIG. 10 shows the mean cytotoxicity from 4 human PBMC samples used as effector cells in an ADCC assay for humanised 2E8 variants and Campath-1H with REH target cells.
Figure 11:
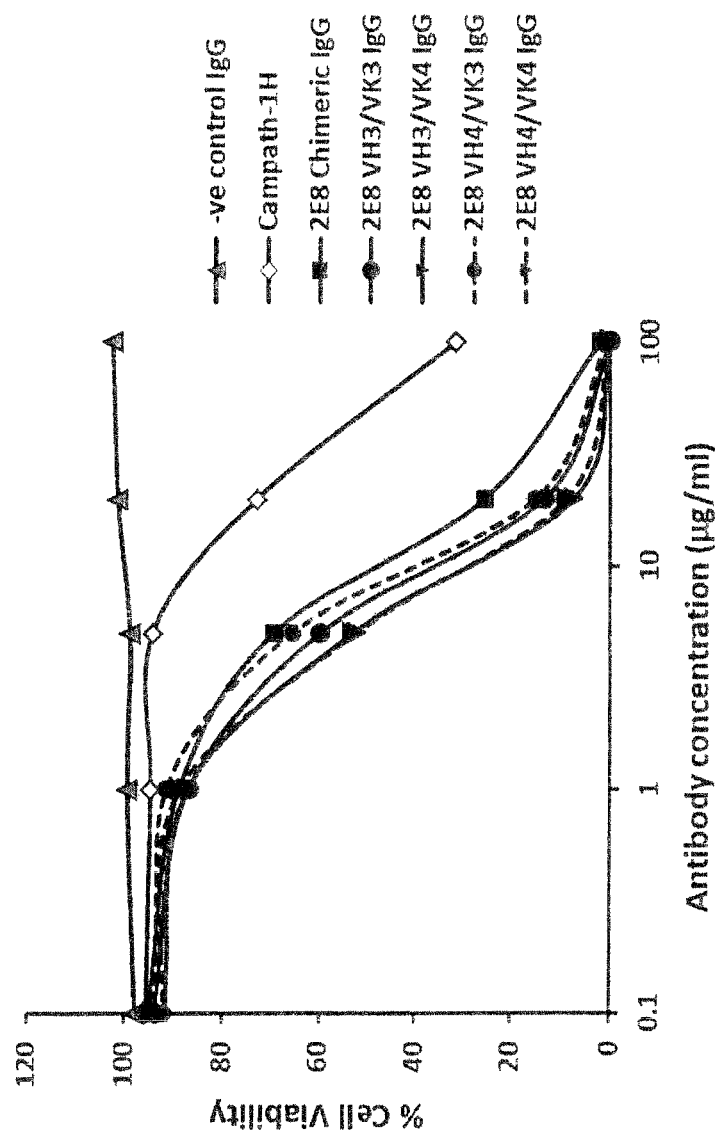
FIG. 11 shows the CDC for humanised 2E8 variants and Campath-1H with high CD52 expressing REH target cells and human complement.
Figure 12:
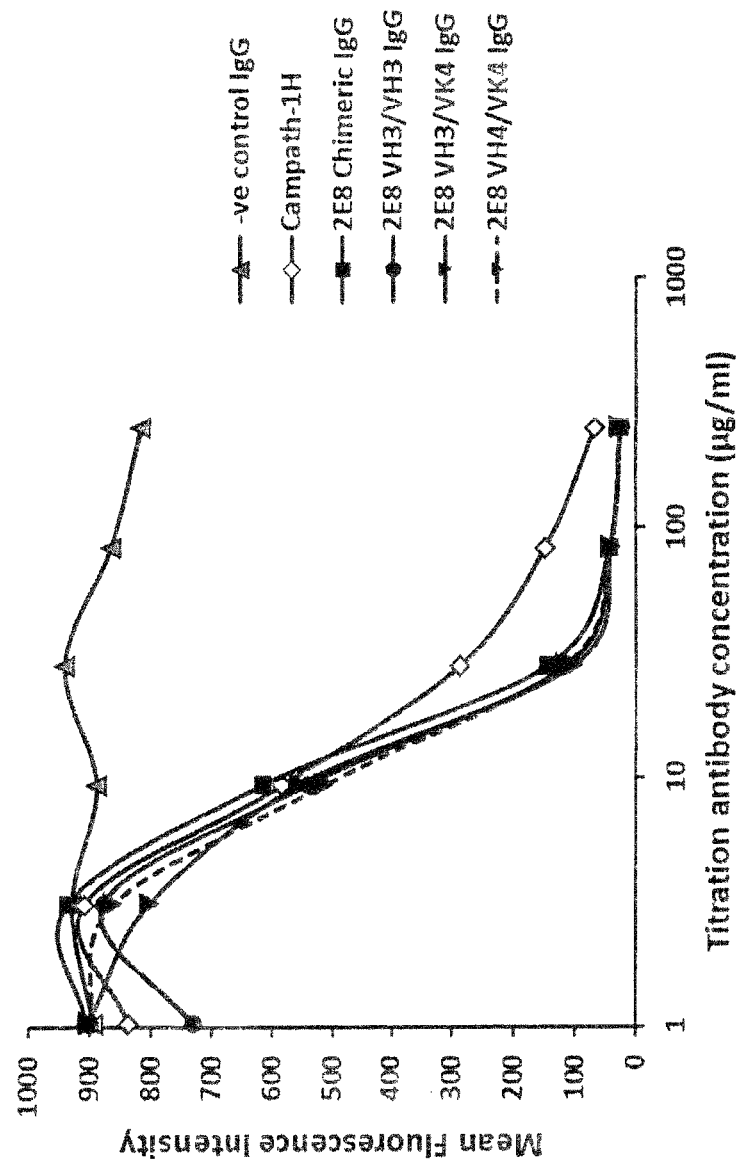
FIG. 12 shows a competition flow cytometry analysis using Campath-1H-PE in competition with chimeric 2E8, Campath-1H and selected variants for binding to REH cells.

As shown in FIG. 8, all lead humanised 2E8 variants displayed competitive binding profiles similar to the parent chimeric antibody. Humanised variants were subsequently tested for binding by flow cytometry as detailed in Example 1, for ADCC as in Example 4, and for CDC as in Example 5. As shown in FIG. 9, the humanised variants exhibited an improved binding profile by flow cytometry to Campath-1H for binding to REH cells. As shown in FIGS. 10 and 11, the humanised variants also exhibited improved ADCC and CDC profile using REH target cells for ADCC at a target:effector cell ratio of 50:1 or the high CD52+ REH cell line for CDC (as in Example 4) compared to Campath-1H.

Example 8

Generation of scFv's And Fab's

Humanised 2E8 variants from Example 6 were converted into scFv's and cloned into M13 phage display vectors as described in Benhar I. and Reiter Y., Current Protocols in Immunology, Unit 10.19B, Wiley Online Library, May 2002 (http://www.currentprotocols.com/protocol/im1019b) using the pCANTAB5E vector RPAS Expression Module (Amersham Pharmacia Biotech, Little Chalfont, UK). Humanised VH and VK genes were amplified using primers which provided terminal SfiI and NotI restriction sites, an internal Gly4Ser linker and a C terminal his6 tag. The scFv constructs were inserted into the pCANTAB5E vector as SfiI-NotI fragments and transformed into E. coli HB2151 resulting in scFv exported to the periplasm and partially to the growth medium. scFv's were purified from growth medium by nickel-chelate affinity chromatography using HIS-Select HF Cartridges (Sigma-Aldrich). Purified 2E8 scFv's were tested in a competition assay as detailed in Example 7 for binding to CD52 peptide and all humanised scFvs exhibited competitive binding to CD52 peptide. Humanised 2E8 variants from Example 6 were also converted into Fab's using the method used for scFv's except that amplified humanised VH and VK genes were further amplified with CH1 and CK constant region genes to form VH-CH1 and VK-Cκ fragments which were further amplified with primers to join these fragments with a 22 amino acid pe1B leader sequence (Lei S. P. et al., J Bacteriol. 169 (1987) p4379-4383) between the upstream VH-CH1 and downstream VK-Cκ gene fragments resulting in a dicistronic Fab gene. Fab's from humanised 2E8 variants were generated and purified as above for scFv's and tested in CD52 peptide competition assay as detailed in Example 7. All humanised Fab's exhibited competitive binding to CD52 peptide.

Example 9

Aalysis of CD4+ T Cell Responses

PBMCs were isolated from healthy community donor buffy coats (from blood drawn within 24 hours) obtained from the UK National Blood Transfusion Service (Addenbrooke's Hospital, Cambridge, UK) and according to approval granted by Addenbrooke's Hospital Local Research Ethics Committee. PBMCs were isolated from buffy coats by Lymphoprep (Axis-shield, Dundee, UK) density centrifugation and $CD8^+$ T cells were depleted using $CD8^+$ Rosette-Sep™ (StemCell Technologies Inc, London, UK). Donors were characterized by identifying HLA-DR haplotypes using an HLA SSP-PCR based tissue-typing kit (Biotest, Solihull, UK). T cell responses to control antigens including the recall antigen tetanus toxin were also determined (KLH Pierce, Cramlingtom, UK and peptides derived from Influenza A and Epstein Barr viruses). PBMC were then frozen and stored in liquid nitrogen until required.

To prepare monocyte derived dendritic cells (DC), 50 different donor PBMCs were selected to provide a distribution with frequencies of HLA-DR and HLA-DQ allotypes similar to the frequencies in the overall world population. PBMCs were revived in AIM-V® culture medium and $CD14^+$ cells isolated using Miltenyi CD14 Microbeads and LS columns (Miltenyi Biotech, Oxford, UK). Monocytes were resuspended in AIM-V® supplemented with 1000 U/ml IL-4 and 1000 U/ml GM-CSF ("DC culture media") to $4$-$6 \times 10^6$ PBMC/ml and then distributed in 24 well plates (2 ml final culture volume). Cells were fed on day 2 by half volume DC culture media change. By day 3, monocytes had differentiated to semi-mature DC which were pre-incubated with either 40 ug/ml of Campath-1H, chimeric 2E8 antibody, humanised 2E8 antibodies, 100 µg/ml KLH or media only. Semi-mature DC were incubated with antigen for 24 hours after which excess test antibody was removed by washing the cells twice and resuspending in DC culture media supplemented with 50 ng/ml TNF-α (Peprotech, London, UK). DCs were fed on day 7 by a half volume DC culture media (supplemented with 50 ng/ml TNFα) change before harvesting mature DC on day 8. The harvested mature DC were counted and viability assessed using trypan blue dye exclusion. The DC were then γ-irradiated (4000 rads) and resuspended at $2 \times 10^5$ cells per ml in AIM-V media before use in the ELISpot and proliferation assays. Additionally, on day 8, fresh CD4+ T cells were also prepared. To purify CD4+ T cells, PBMCs were revived in AIM-V® culture medium and $CD4^+$ cells isolated using Miltenyi CD4 Microbeads and LS columns (Miltenyi Biotech, Oxford, UK) and resuspended in AIM-V® media at $2 \times 10^6$ cells/ml.

On day 8, T cell proliferation assays were established whereby $1 \times 10^5$ autologous $CD4^+$ T cells were added to $1 \times 10^4$ humanised 2E8 or chimeric 2E8 antibody loaded DC (ratio of 10:1) in 96 well U-bottomed plates, with AIM-V® media added to a final volume 200 ul/well). On day 14, assay plates were pulsed with 1 uCi [3H] (Perkin Elmer, Beaconsfield, UK) per well in 25 ul AIMV for 6 hours before harvesting onto filter mats (Perkin Elmer) using a TomTec Mach III (Hamden Conn., USA) cell harvester. Counts per minute (cpm) for each well were determined by Meltilex™ (Perkin Elmer) scintillation counting on a 1450 Microbeta Wallac Trilux Liquid Scintillation Counter (Perkin Elmer) in paralux, low background counting. Counts per minute for each antibody sample were normalised to the media only control.

For ELISpot assays, ELISpot plates (Millipore, Watford, UK) were coated with 100 µl/well IL-2 capture antibody (R&D Systems, Abingdon, UK) in PBS. Plates were then washed twice in PBS, incubated overnight in block buffer (1% BSA (Sigma) in PBS) and washed in AIM V® medium. On day 8, $1 \times 10^5$ autologous $CD4^+$ T cells were added to $1 \times 10^4$ antigen loaded DC (ratio of 10:1) in 96 well ELISpot plates. All preparations were tested in sextuplet cultures. For each donor PBMC, a negative control (AIM V® medium alone), no cells control and a PHA (10 ug/ml) positive control were also included.

After a further 7 day incubation period, ELISpot plates were developed by three sequential washes in $dH_2O$ and PBS prior to the addition of 100 µl filtered biotinylated detection antibody (R&D Systems, Abingdon, UK) in PBS/1% BSA. Following incubation at 37° C. for 1.5 hour, plates were further washed three times in PBS and 100 µl filtered streptavidin-AP (R&D Systems) in PBS/1% BSA was added for 1 hour (incubation at room temperature).

Streptavidin-AP was discarded and plates were washed four times in PBS. BCIP/NBT (R&D Systems) was added to each well and incubated for 30 minutes at room temperature. Spot development was stopped by washing the wells and the backs of the wells three times with $dH_2O$. Dried plates were scanned on an Immunoscan™ Analyser and spots per well (spw) were determined using Immunoscan™ Version 4 software.

For both proliferation and IL-2 ELISpot assays, results were expressed as a Stimulation Index (SI) defined as the ratio of cpm (proliferation assay) or spots (ELISpot assay) for the test antibody against a medium-only control using a threshold of SI equal to or greater than 2 (SI≥2.0) for positive T cell responses. The data showed that both Campath-1H and chimeric 2E8 antibody induced T cell responses in 10 or more of the 50 donor PBMCs tested (>=20%) whilst none of the humanised 2E8 antibodies induced T cell responses in more than 2 of 50 donors (<=4%) demonstrating the effectiveness of the humanisation process in removing T cell responses from the V regions.

Example 10

Direct Cytoxicity Assay

Figure 13A:
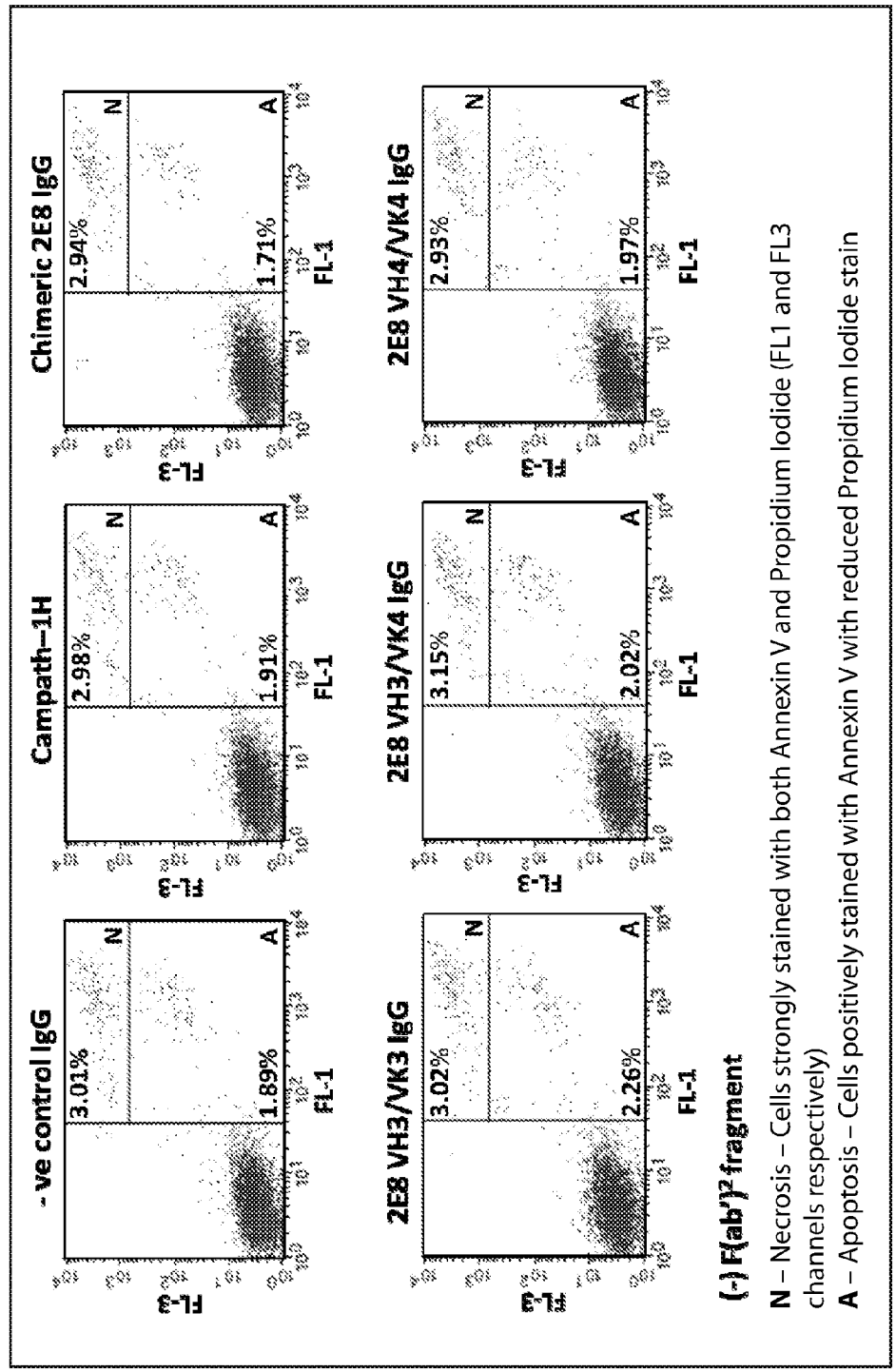
FIGS. 13A-13B show the direct cytotoxic effects of anti-human CD52 antibodies on REH cells as measured by apoptosis and necrosis.
Figure 13B:
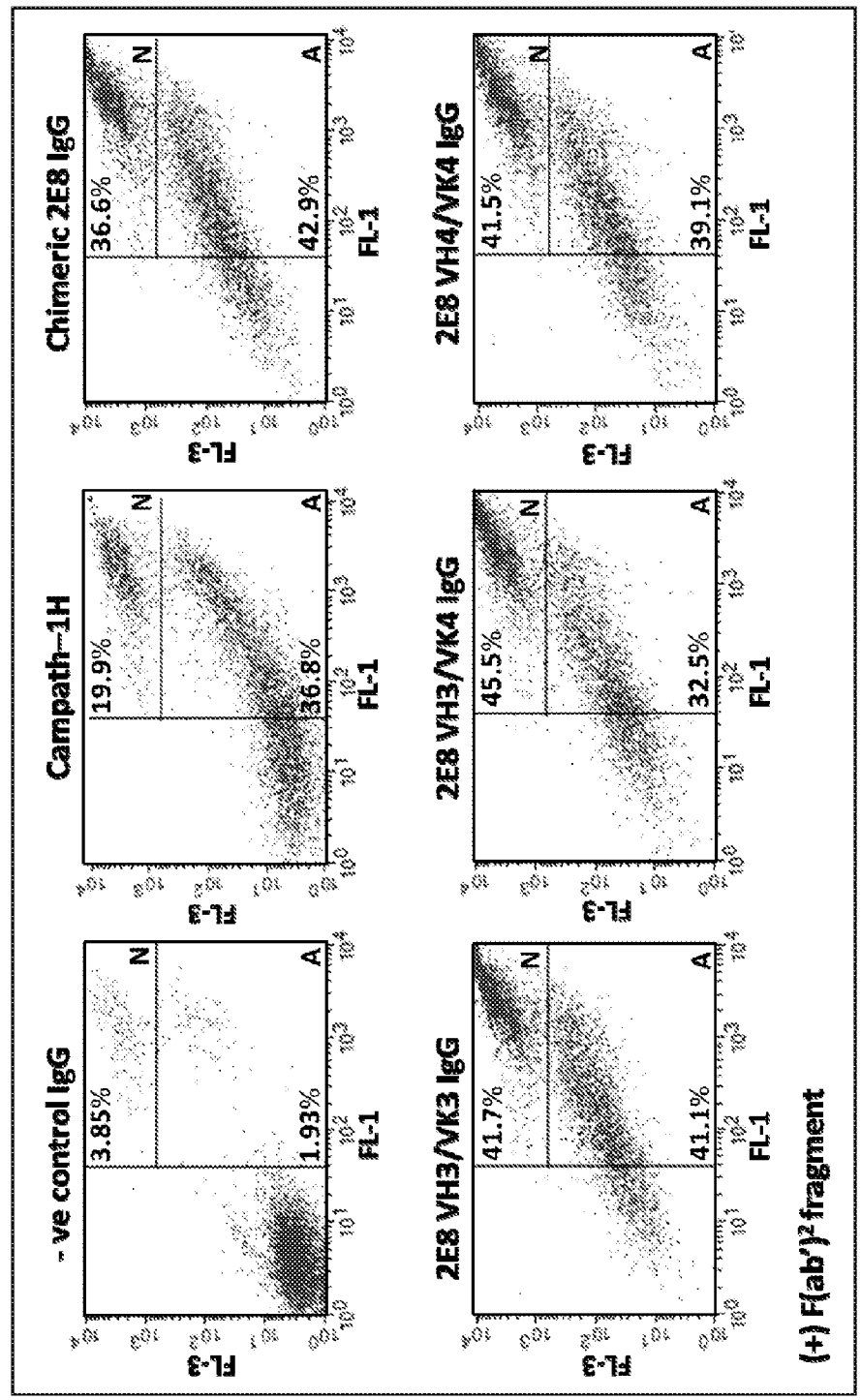

Direct cytotoxic effects of anti-human CD52 antibodies were assessed using Annexin V/Propidium Iodide co-staining as markers of apoptosis and necrosis respectively. $1 \times 10^5$ REH cells were plated in the presence of 100 µg/ml anti-human CD52 test antibodies or an isotype matched control antibody +/−100 µg/ml F(ab')$^2$ crosslinking antibody (Jackson ImmunoResearch, Cat no. 109-006-008) (600 ul final vol). Cells were incubated for 72 hrs before washing in PBS/2% BSA followed by co-staining with Annexin V/Propidium Iodide according to manufacturers recommended protocol (Invitrogen, Cat no. V13245). Scatterplots were generated using FACS analysis and divided into three regions for quantitation of live cells (unstained), apoptotic cells (FL1, Annexin V positive) and necrotic cells (FL1, Annexin V positive & FL3, Propidium Iodide positive). As shown in FIGS. 13A and 13B, the humanised 2E8 antibodies exhibited increased apoptosis and necrosis compared to Campath-1H of REH target cells, with % necrotic cells of >40% from the humanised antibodies compared to 19.9% for Campath-1H.

Example 11

Tumour Animal Model

Figure 14:
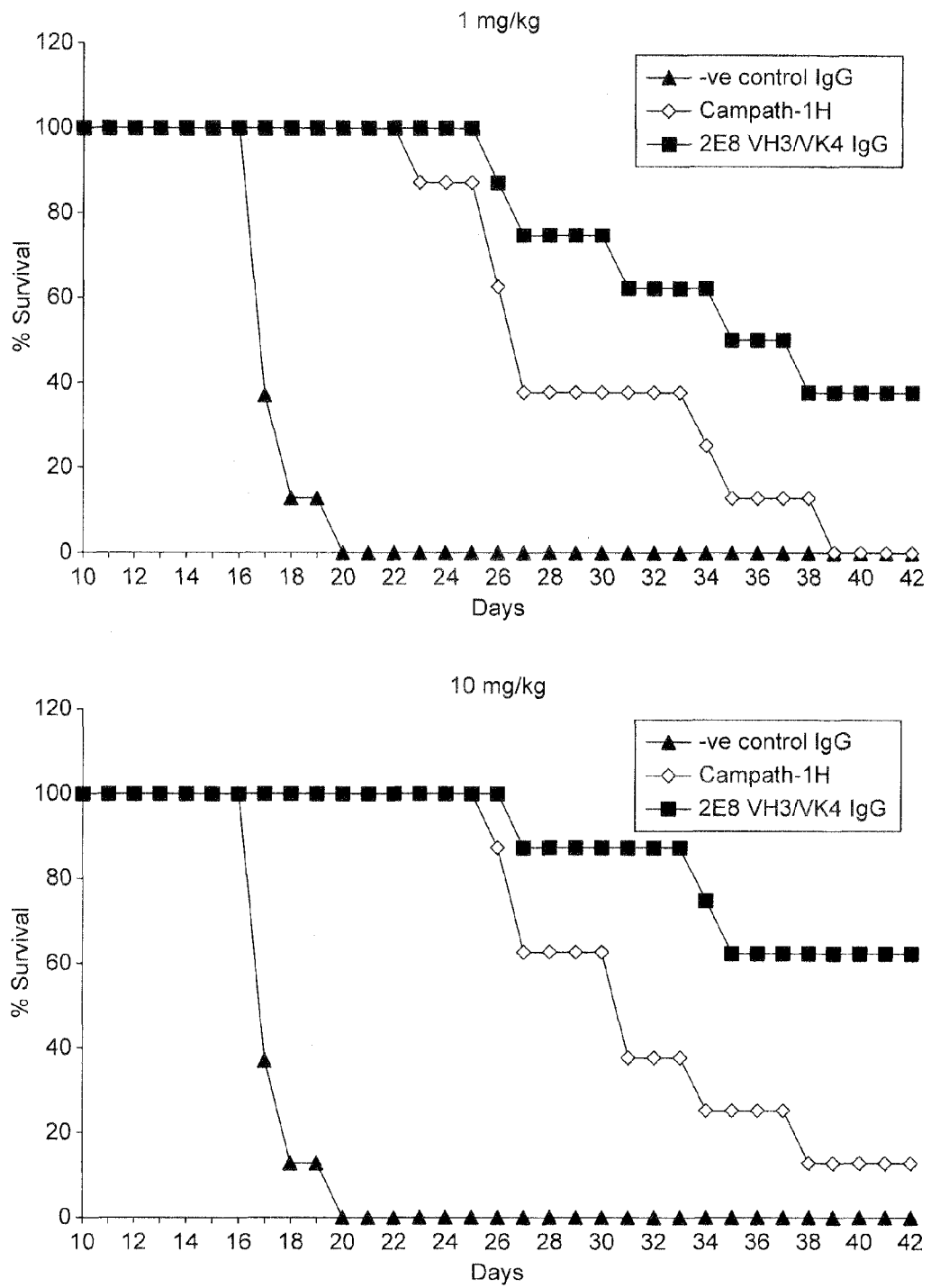
FIG. 14 shows the Kaplan-Meier plot for SCID mice transplanted with Raji human Burkitt lymphoma cells following treatment with Campath-1H and the lead humanised 2E8 variant VH3/VK4 (V region SEQ ID NOS. 22 and 28).

A tumour animal model was used for in vivo analysis of anti-human CD52 antibodies in inhibiting tumour growth. In the model, Raji human Burkitt lymphoma cells were transplanted into SCID mice and the animals treated with anti-human CD52 antibodies. 7 week old female Fox Chase SCID Mice (Charles River, Morrisville, N.C., USA) were injected with $1 \times 10^6$ Raji cells (American Type Culture Collection, 0.2 mL cell suspension) via a bolus tail-vein (i.v.) injection. Anti-human CD52 test antibodies or an isotype matched control antibody were each administered intraperitoneally (i.p.) once daily on alternate days for seven doses, starting three days after tumour cell injection. The dosing volume of 10 mL/kg (0.20 mL/20 g mouse) was scaled to the body weight of each animal, as determined twice weekly. The results shown in FIG. 14 demonstrated an improved survival rate at both 1 and 10 mg/kg doses by the lead VH3/VK4 anti-CD52 antibody (V region SEQ IDs: 22 and 28) compared to Campath 1H.

```
                              Sequences

>SEQ ID No. 1
2E8 Mouse VH DNA
GAGGTGCACCTGATGGAGTCTGGGGGAGGCTTAGTGCAGCCTGGAGGGTCCCTGAGACTCTCCTGTGC

AGCCTCTGGATTCACTTTCAGTAGGTATGGCATGTCTTGGGTTCGCCAGACTCCAGACAAGAGGCTGG

AGTTGGTCGCAATGATGAAAACTAAAGGTGGTAGGACCTATTATCCAGACAGTGTGAAGGGCCGATTC

ACCATTTCCAGAGACAATGCCAAGAACTCCCTGTACCTGCAAATGAGCAGTCTGAAGTCTGAGGACAC

AGCCATCTATTTCTGTGCAAGTGATGGTTACTACTGGGGCCAAGGCACCACTCTCACAGTCTCCTCA

>SEQ ID No. 2
2E8 Mouse VK DNA
GATGTTTTGATGACCCAGACTCCACTCACTTTGTCGGTAACCATTGGACAACCAGCCTCCATCTCTTGC

AAGTCAAGTCAGAGCCTCTTACATAGTGATGGAAAGACATATTTGAATTGGTTGTTACAGAGGCCAGG

CCAGTCTCCAAAGCGCCTAATCTATCTGGTGTCTAAACTGGACTCTGGAGTCCCTGACAGGTTCACTGG

CAGTGGATCAGGGACAGATTTCACACTGAAAATCAGCAGAGTGGAGGCTGAGGATTTGGGAATTTATT

ATTGCTGGCAAGGTACACATTTGTGGACGTTCGGTGGAGGCACCAAACTGGAAATCAAA

>SEQ ID No. 3
2E8 Mouse VH amino acid
EVHLMESGGGLVQPGGSLRLSCAASGFTESRYGMSWVRQTPDKRLELVAMMKTKGGRTYYPDSVKGRFT

ISRDNAKNSLYLQMSSLKSEDTAIYFCASDGYYWGQGTTLTVSS

>SEQ ID No. 4
2E8 Mouse VK amino acid
DVLMTQTPLTLSVTIGQPASISCKSSQSLLHSDGKTYLNWLLQRPGQSPKRLIYLVSKLDSGVPDRFTGSGS

GTDFTLKISRVEAEDLGIYYCWQGTHLWTEGGGTKLEIK

>SEQ ID No. 5
2E8 VH CDR1 amino acid
RYGMS

>SEQ ID No. 6
2E8 VH CDR2 amino acid
MMKTKGGRTYYPDSVKG

>SEQ ID No. 7
2E8 VH CDR3 amino acid
DGYY

>SEQ ID No. 8
2E8 VK CDR1 amino acid
KSSQSLLHSDGKTYLN

>SEQ ID No. 9
2E8 VK CDR2 amino acid
LVSKLDS
```

| Sequences |
|---|
| >SEQ ID No. 10<br>2E8 VK CDR3 amino acid<br>WQGTHLWT<br><br>>SEQ ID No. 11<br>2E8 Humanised VH Variant 1 DNA<br>GAGGTGCACCTGGTGGAATCCGGCGGAGGACTGGTGCAGCCTGGCGGCTCCCTGAGACTGTCTTGCGCCGCCTC<br><br>CGGCTTCACCTTCTCCAGATACGGCATGTCCTGGGTCCGACAGGCCCCTGGCAAGGGCCTGGAACTGGTGGCCA<br><br>TGATGAAGACCAAGGGCGGCAGAACCTACTACCCCGACTCCGTGAAGGGCCGGTTCACCATCTCCCGGGACAAC<br><br>GCCAAGAACTCCCTGTACCTGCAGATGTCCTCCCTGAAGGCCGAGGACACCGCCATCTACTTTTGCGCCTCCGA<br><br>CGGCTACTACTGGGGCCAGGGCACCACCGTGACCGTGTCATCA<br><br>>SEQ ID No. 12<br>2E8 Humanised VH Variant 2 DNA<br>GAGGTGCACCTGGTGGAATCCGGCGGAGGACTGGTGCAGCCTGGCGGCTCCCTGAGACTGTCTTGCGCCGCCTC<br><br>CGGCTTCACCTTCTCCAGATACGGCATGTCCTGGGTCCGACAGGCCCCTGGCAAGGGCCTGGAACTGGTGGCCA<br><br>TGATGAAGACCAAGGGCGGCAGAACCTACTACCCCGACTCCGTGAAGGGCCGGTTCACCATCTCCCGGGACAAC<br><br>GCCAAGAACTCCCTGTACCTGCAGATGAACTCCCTGCGGGCCGAGGACACCGCCATCTACTTTTGCGCCTCCGA<br><br>CGGCTACTACTGGGGCCAGGGCACCACCGTGACCGTGTCATCA<br><br>>SEQ ID No. 13<br>2E8 Humanised VH Variant 3 DNA<br>GAGGTGCACCTGGTGGAATCCGGCGGAGGACTGGTGCAGCCTGGCGGCTCCCTGAGACTGTCTTGCGCCGCCTC<br><br>CGGCTTCACCTTCTCCAGATACGGCATGTCCTGGGTCCGACAGGCCCCTGGCAAGGGCCTGGAACTGGTGGCCA<br><br>TGATGAAGACCAAGGGCGGCAGAACCTACTACCCCGACTCCGTGAAGGGCCGGTTCACCATCTCCCGGGACAAC<br><br>GCCAAGAACTCCCTGTACCTGCAGATGAACTCCCTGCGGGCCGAGGACACCGCCATCTACTACTGCGCCTCCGA<br><br>CGGCTACTACTGGGGCCAGGGCACCACCGTGACCGTGTCATCA<br><br>>SEQ ID No. 14<br>2E8 Humanised VH Variant 4 DNA<br>GAGGTGCACCTGGTGGAATCCGGCGGAGGACTGGTGCAGCCTGGCGGCTCCCTGAGACTGTCTTGCGCCGCCTC<br><br>CGGCTTCACCTTCTCCAGATACGGCATGTCCTGGGTCCGACAGGCCCCTGGCAAGGGCCTGGAACTGGTGGCCA<br><br>TGATGAAGACCAAGGGCGGCAGAACCTACTACCCCGACTCCGTGAAGGGCCGGTTCACCATCTCCCGGGACAAC<br><br>GCCAAGAACTCCCTGTACCTGCAGATGAACTCCCTGCGGGCCGAGGACACCGCCGTGTACTACTGCGCCTCCGA<br><br>CGGCTACTACTGGGGCCAGGGCACCACCGTGACCGTGTCATCA<br><br>>SEQ ID No. 15<br>2E8 Humanised VH Variant 5 DNA<br>GAGGTGCACCTGGTGGAATCCGGCGGAGGACTGGTGCAGCCTGGCGGCTCCCTGAGACTGTCTTGCGCCGCCTC<br><br>CGGCTTCACCTTCTCCAGATACGGCATGTCCTGGGTCCGACAGGCCCCTGGCAAGGGACTGGAATGGTGGCCA<br><br>TGATGAAGACCAAGGGCGGCAGAACCTACTACCCCGACTCCGTGAAGGGCCGGTTCACCATCTCCCGGGACAAC<br><br>GCCAAGAACTCCCTGTACCTGCAGATGAACTCCCTGCGGGCCGAGGACACCGCCATCTACTACTGCGCCTCCGA<br><br>CGGCTACTACTGGGGCCAGGGCACCACCGTGACCGTGTCATCA<br><br>>SEQ ID No. 16<br>2E8 Humanised VK Variant 1 DNA<br>GACGTGCTGATGACCCAGACCCCCCTGACCCTGTCCGTGACCCTGGGCCAGCCTGCCTCCATCTCCTGCAAGTC<br><br>CTCCCAGTCCCTGCTGCACTCCGACGGCAAGACCTACCTGAACTGGCTGCAGCAGCGGCCTGGCCAGTCCCCCA<br><br>AGCGGCTGATCTACCTGGTGTCCAAGCTGGACTCCGGCGTGCCCGACAGATTCACCGGCTCTGGCTCCGGCACC<br><br>GACTTCACCCTGAAGATCTCCCGGGTGGAAGCCGAGGACGTGGGCATCTACTACTGCTGGCAGGGCACCCATCT<br><br>GTGGACCTTCGGCGGAGGCACAAAGGTGGAAATCAAA |

-continued

Sequences

>SEQ ID No. 17
2E8 Humanised VK Variant 2 DNA
GACGTGCTGATGACCCAGACCCCCCTGACCCTGTCCGTGACCCTGGGCCAGCCTGCCTCCATCTCCTGCAAGTC

CTCCCAGTCCCTGCTGCACTCCGACGGCAAGACCTACCTGAACTGGCTGCAGCAGCGGCCTGGCCAGTCTCCTC

GGCGGCTGATCTACCTGGTGTCCAAGCTGGACTCCGGCGTGCCCGACAGATTCACCGGCTCTGGCTCCGGCACC

GACTTCACCCTGAAGATCTCCCGGGTGGAAGCCGAGGACGTGGGCATCTACTACTGCTGGCAGGGCACCCATCT

GTGGACCTTCGGCGGAGGCACAAAGGTGGAAATCAAA

>SEQ ID No. 18
2E8 Humanised VK Variant 3 DNA
GACGTGCTGATGACCCAGACCCCCCTGTCCCTGTCCGTGACCCTGGGCCAGCCTGCCTCCATCTCCTGCAAGTC

CTCCCAGTCCCTGCTGCACTCCGACGGCAAGACCTACCTGAACTGGCTGCAGCAGCGGCCTGGCCAGTCTCCTC

GGCGGCTGATCTACCTGGTGTCCAAGCTGGACTCCGGCGTGCCCGACAGATTCACCGGCTCTGGCTCCGGCACC

GACTTCACCCTGAAGATCTCCCGGGTGGAAGCCGAGGACGTGGGCATCTACTACTGCTGGCAGGGCACCCATCT

GTGGACCTTCGGCGGAGGCACAAAGGTGGAAATCAAA

>SEQ ID No. 19
2E8 Humanised VK Variant 4 DNA
GACGTGGTGATGACCCAGACCCCCCTGTCCCTGTCCGTGACCCTGGGCCAGCCTGCCTCCATCTCCTGCAAGTC

CTCCCAGTCCCTGCTGCACTCCGACGGCAAGACCTACCTGAACTGGCTGCAGCAGCGGCCTGGCCAGTCTCCTC

GGCGGCTGATCTACCTGGTGTCCAAGCTGGACTCCGGCGTGCCCGACAGATTCTCCGGCTCTGGCTCCGGCACC

GACTTCACCCTGAAGATCTCCCGGGTGGAAGCCGAGGACGTGGGCATCTACTACTGCTGGCAGGGCACCCATCT

GTGGACCTTCGGCGGAGGCACAAAGGTGGAAATCAAA

>SEQ ID No. 20
2E8 Humanised VH Variant 1 amino acid
EVHLVESGGGLVQPGGSLRLSCAASGFTFSRYGMSWVRQAPGKGLELVAMMKTKGGRTYYPDSVKGRFTISRDNAKNS

LYLQMSSLKAEDTAIYFCASDGYYWGQGTTVTVSS

>SEQ ID No. 21
2E8 Humanised VH Variant 2 amino acid
EVHLVESGGGLVQPGGSLRLSCAASGFTFSRYGMSWVRQAPGKGLELVAMMKTKGGRTYYPDSVKGRFTISRDNAKNS

LYLQMNSLRAEDTAIYFCASDGYYWGQGTTVTVSS

>SEQ ID No. 22
2E8 Humanised VH Variant 3 amino acid
EVHLVESGGGLVQPGGSLRLSCAASGFTFSRYGMSWVRQAPGKGLELVAMMKTKGGRTYYPDSVKGRFTISRDNAKNS

LYLQMNSLRAEDTAIYYCASDGYYWGQGTTVTVSS

>SEQ ID No. 23
2E8 Humanised VH Variant 4 amino acid
EVHLVESGGGLVQPGGSLRLSCAASGFTFSRYGMSWVRQAPGKGLELVAMMKTKGGRTYYPDSVKGRFTISRDNAKNS

LYLQMNSLRAEDTAVYYCASDGYYWGQGTTVTVSS

>SEQ ID No. 24
2E8 Humanised VH Variant 5 amino acid
EVHLVESGGGLVQPGGSLRLSCAASGFTFSRYGMSWVRQAPGKGLEWVAMMKTKGGRTYYPDSVKGRFTISRDNAKN

SLYLQMNSLRAEDTAIYYCASDGYYWGQGTTVTVSS

>SEQ ID No. 25
2E8 Humanised VK Variant 1 amino acid
DVLMTQTPLTLSVTLGQPASISCKSSQSLLHSDGKTYLNWLQQRPGQSPKRLIYLVSKLDSGVPDRFTGSGSGTDFTLKISR

VEAEDVGIYYCWQGTHLWTFGGGTKVEIK

>SEQ ID No. 26
2E8 Humanised VK Variant 2 amino acid
DVLMTQTPLTLSVTLGQPASISCKSSQSLLHSDGKTYLNWLQQRPGQSPRRLIYLVSKLDSGVPDRFTGSGSGTDFTLKISR

VEAEDVGIYYCWQGTHLWTFGGGTKVEIK

| Sequences |
|---|

>SEQ ID No. 27
2E8 Humanised VK Variant 3 amino acid
DVLMTQTPLSLSVTLGQPASISCKSSQSLLHSDGKTYLNWLQQRPGQSPRRLIYLVSKLDSGVPDRFTGSGSGTDFTLKISR

VEAEDVGIYYCWQGTHLWTFGGGTKVEIK

>SEQ ID No. 28
2E8 Humanised VK Variant 4 amino acid
DVVMTQTPLSLSVTLGQPASISCKSSQSLLHSDGKTYLNWLQQRPGQSPRRLIYLVSKLDSGVPDRFSGSGSGTDFTLKIS

RVEAEDVGIYYCWQGTHLWTFGGGTKVEIK

The invention claimed is:

1. An anti-CD52 antibody or antigen-bending portion thereof comprising at least three CDR sequences:
   (i) CDRH1 comprising sequence RYGMS (SEQ ID NO: 5),
   (ii) CDRH2 comprising sequence MMKTKGGRTYYP-DSVKG (SEQ ID NO: 6), and
   (iii) CDRH3 comprising sequence DGYY (SEQ ID NO: 7); or
   (iv) CDRL1 comprising sequence KSSQSLLHSDGK-TYLN (SEQ ID NO: 8),
   (v) CDRL2 comprising sequence LVSKLDS (SEQ ID NO: 9), and
   (vi) CDRL3 comprising sequence WQGTHLWT (SEQ ID NO: 10).

2. An anti-CD52 antibody or antigen-binding portion thereof comprising one or more variable region sequences selected from the group consisting of SEQ ID NOS: 20-24 for the heavy chain variable region in combination with one or more sequences selected from the group consisting of SEQ ID NOS: 25-28 for the light chain variable region.

3. An anti-CD52 antibody or antigen-binding portion thereof comprising SEQ ID NO: 22 for the heavy chain variable region in combination with SEQ ID NO: 28 for the light chain variable region.

4. The anti-CD52 antibody or antigen-binding portion thereof of claim 1 which, when tested in vitro for induction of CD4+helper T cell responses in 50 human blood samples with a distribution of HLA-DR allotypes from the human population, gives rise to <=4% of T cell responses.

5. The antibody or antigen-binding portion thereof of claim 1 where variable region sequences are entirely derived from sequences in human antibody variable regions.

6. The antibody of claim 5 which is comprised of variable regions together with human constant regions.

7. The antibody of claim 6 where the human heavy chain constant region is either isotype IgG1, IgG2, IgG3 or IgG4, or a mutated IgG constant region, and the human light chain human constant region is isotype kappa.

8. The antibody of claim 6 where the human constant regions are isotypes IgG1 and kappa, or isotypes IgG4 and kappa.

9. The antibody or antigen-binding portion thereof of of claim 1 where the antigen-binding portion is a scFv or Fab.

10. A polynucleotide encoding the antibody or antigen-binding portion thereof of claim 1.

11. A vector comprising the polynucleotide of claim 10.

12. A host cell comprising a vector of claim 11.

13. A composition comprising the anti-CD52 antibody or antigen-binding portion thereof of claim 1, a polynucleotide encoding the antibody, or antigen-binding portion thereof, or a vector comprising the polynucleotide.

14. A method for treating a disease selected from the group consisting of chronic lymphocytic leukemia (CLL), other leukemias, multiple sclerosis, rheumatoid arthritis, vasculitis, myositis, diabetes, other autoimmune diseases, organ transplant rejection, and graft-vs-host disease; said method comprising administering an effective amount of (i) the antibody or antigen-binding portion thereof of claim 1, (ii) a polynucleotide encoding the antibody or antigen-binding portion thereof, or (iii) a composition comprising the antibody or antigen-binding portion thereof, the polynucleotide, or a vector comprising the polynucleotide to a subject in need of such treatment.

15. The method of claim 14 which further comprises co-administering an effective amount of a chemotherapeutic agent.

16. The method of claim 14 which further comprises co-administering a pharmaceutical carrier.

17. A method using the antibody or antigen-binding portion thereof of claim 1, said method comprising;
  (a) contacting a test sample with the antibody or antigen-binding portion thereof under conditions that allow for formation of a complex between human CD52 antigen and the antibody or antigen-binding portion thereof, and
  (b) detecting the presence of the complex.

18. An anti-CD52 antibody or antigen-binding portion thereof comprising at least six CDR sequences:
  (i) CDRH1 comprising sequence RYGMS (SEQ ID NO: 5),
  (ii) CDRH2 comprising sequence MMKTKGGRTYYPDSVSKG (SEQ ID NO: 6),
  (iii) CDRH3 comprising sequence DGYY (SEQ ID NO: 7),
  (iv) CDRL1 comprising sequence KSSQSLLHSDGKTYLN (SEQ ID NO: 8),
  (v) CDRL2 comprising sequence LVSKLDS (SEQ ID NO: 9), and
  (vi) CDRL3 comprising sequence WQGTHLWT (SEQ ID NO: 10).

19. A polynucleotide encoding the antibody or antigen-binding portion thereof of claim 18.

20. A vector comprising the polynucleotide of claim 19.

21. A host cell comprising a vector of claim 20.

* * * * *

SEQUENCE LISTING

<160> NUMBER OF SEQ ID NOS: 28

<210> SEQ ID NO 1
<211> LENGTH: 339
<212> TYPE: DNA
<213> ORGANISM: Mus musculus
<220> FEATURE:
<223> OTHER INFORMATION: 2E8 Mouse VH DNA

<400> SEQUENCE: 1

```
gaggtgcacc tgatggagtc tgggggaggc ttagtgcagc ctggagggtc cctgagactc      60
tcctgtgcag cctctggatt cactttcagt aggtatggca tgtcttgggt tcgccagact     120
ccagacaaga ggctggagtt ggtcgcaatg atgaaaacta aggtggtag gacctattat      180 ccagacagtg tgaagggccg attcaccatt tccagagaca tgccaagaa ctccctgtac      240 ctgcaaatga gcagtctgaa gtctgaggac acagccatct atttctgtgc aagtgatggt     300
tactactggg gccaaggcac cactctcaca gtctcctca                            339
```

<210> SEQ ID NO 2
<211> LENGTH: 333
<212> TYPE: DNA
<213> ORGANISM: Mus musculus
<220> FEATURE:
<223> OTHER INFORMATION: 2E8 Mouse VK DNA

<400> SEQUENCE: 2

```
gatgttttga tgacccagac tccactcact ttgtcggtaa ccattggaca accagcctcc      60
atctcttgca agtcaagtca gagcctctta catagtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggaatt tattattgct ggcaaggtac acatttgtgg     300
acgttcggtg aggcaccaa actggaaatc aaa                                   333
```

<210> SEQ ID NO 3
<211> LENGTH: 113
<212> TYPE: PRT
<213> ORGANISM: Mus musculus
<220> FEATURE:
<223> OTHER INFORMATION: 2E8 Mouse VH

<400> SEQUENCE: 3

Glu Val His Leu Met Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Thr Pro Asp Lys Arg Leu Glu Leu Val
        35                  40                  45

Ala Met Met Lys Thr Lys Gly Gly Arg Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Lys Ser Glu Asp Thr Ala Ile Tyr Phe Cys
                85                  90                  95

Ala Ser Asp Gly Tyr Tyr Trp Gly Gln Gly Thr Thr Leu Thr Val Ser
            100                 105                 110

Ser

<210> SEQ ID NO 4
<211> LENGTH: 111
<212> TYPE: PRT
<213> ORGANISM: Mus musculus
<220> FEATURE:
<223> OTHER INFORMATION: 2E8 Mouse VK

<400> SEQUENCE: 4

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Leu Trp Thr Phe Gly Gly Gly Thr Lys Leu Glu Ile Lys
            100                 105                 110

<210> SEQ ID NO 5
<211> LENGTH: 5
<212> TYPE: PRT
<213> ORGANISM: Artificial Sequence
<220> FEATURE:
<223> OTHER INFORMATION: 2E8 VH CDR1 Peptide

<400> SEQUENCE: 5

Arg Tyr Gly Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: 2E8 VH CDR2 Peptide

<400> SEQUENCE: 6

Met Met Lys Thr Lys Gly Gly Arg Thr Tyr Tyr Pro Asp Ser Val Lys
1               5                   10                  15

Gly

```
<210> SEQ ID NO 7
<211> LENGTH: 4
<212> TYPE: PRT
<213> ORGANISM: Artificial Sequence
<220> FEATURE:
<223> OTHER INFORMATION: 2E8 VH CDR3 Peptide

<400> SEQUENCE: 7

Asp Gly Tyr Tyr
1

<210> SEQ ID NO 8
<211> LENGTH: 16
<212> TYPE: PRT
<213> ORGANISM: Artificial Sequence
<220> FEATURE:
<223> OTHER INFORMATION: 2E8 VK CDR1 Peptide

<400> SEQUENCE: 8

Lys Ser Ser Gln Ser Leu Leu His Ser Asp Gly Lys Thr Tyr Leu Asn
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: 2E8 VK CDR2 Peptide

<400> SEQUENCE: 9

Leu Val Ser Lys Leu Asp Ser
1               5

<210> SEQ ID NO 10
<211> LENGTH: 8
<212> TYPE: PRT
<213> ORGANISM: Artificial Sequence
<220> FEATURE:
<223> OTHER INFORMATION: 2E8 VK CDR3 Peptide

<400> SEQUENCE: 10

Trp Gln Gly Thr His Leu Trp Thr
1               5

<210> SEQ ID NO 11
<211> LENGTH: 339
<212> TYPE: DNA
<213> ORGANISM: Artificial Sequence
<220> FEATURE:
<223> OTHER INFORMATION: 2E8 Humanised VH Variant 1 Synthetic DNA

<400> SEQUENCE: 11
gaggtgcacc tggtggaatc cggcggagga ctggtgcagc ctggcggctc cctgagactg      60
tcttgcgccg cctccggctt caccttctcc agatacggca tgtcctgggt ccgacaggcc    120
cctggcaagg gcctggaact ggtggccatg atgaagacca agggcggcag aacctactac    180
cccgactccg tgaagggccg gttcaccatc tcccgggaca cgccaagaa ctccctgtac     240 ctgcagatgt cctccctgaa ggccgaggac accgccatct actttgcgc ctccgacggc     300 tactactggg gccagggcac caccgtgacc gtgtcatca                            339

<210> SEQ ID NO 12
<211> LENGTH: 339
<212> TYPE: DNA
<213> ORGANISM: Artificial Sequence
```

```
<220> FEATURE:
<223> OTHER INFORMATION: 2E8 Humanised VH Variant 2 Synthetic DNA

<400> SEQUENCE: 12
gaggtgcacc tggtggaatc cggcggagga ctggtgcagc ctggcggctc cctgagactg      60
tcttgcgccg cctccggctt caccttctcc agatacggca tgtcctgggt ccgacaggcc     120
cctggcaagg gcctggaact ggtggccatg atgaagacca agggcggcag aacctactac     180
cccgactccg tgaagggccg gttcaccatc tcccgggaca cgccaagaa ctccctgtac      240 ctgcagatga actccctgcg ggccgaggac accgccatct acttttgcgc ctccgacggc     300
tactactggg gccagggcac caccgtgacc gtgtcatca                             339

<210> SEQ ID NO 13
<211> LENGTH: 339
<212> TYPE: DNA
<213> ORGANISM: Artificial Sequence
<220> FEATURE:
<223> OTHER INFORMATION: 2E8 Humanised VH Variant 3 Synthetic DNA

<400> SEQUENCE: 13
gaggtgcacc tggtggaatc cggcggagga ctggtgcagc ctggcggctc cctgagactg      60
tcttgcgccg cctccggctt caccttctcc agatacggca tgtcctgggt ccgacaggcc     120
cctggcaagg gcctggaact ggtggccatg atgaagacca agggcggcag aacctactac     180
cccgactccg tgaagggccg gttcaccatc tcccgggaca cgccaagaa ctccctgtac      240 ctgcagatga actccctgcg ggccgaggac accgccatct actactgcgc ctccgacggc     300
tactactggg gccagggcac caccgtgacc gtgtcatca                             339

<210> SEQ ID NO 14
<211> LENGTH: 339
<212> TYPE: DNA
<213> ORGANISM: Artificial Sequence
<220> FEATURE:
<223> OTHER INFORMATION: 2E8 Humanised VH Variant 4 Synthetic DNA

<400> SEQUENCE: 14
gaggtgcacc tggtggaatc cggcggagga ctggtgcagc ctggcggctc cctgagactg      60
tcttgcgccg cctccggctt caccttctcc agatacggca tgtcctgggt ccgacaggcc     120
cctggcaagg gcctggaact ggtggccatg atgaagacca agggcggcag aacctactac     180
cccgactccg tgaagggccg gttcaccatc tcccgggaca cgccaagaa ctccctgtac      240 ctgcagatga actccctgcg ggccgaggac accgccgtgt actactgcgc ctccgacggc     300
tactactggg gccagggcac caccgtgacc gtgtcatca                             339

<210> SEQ ID NO 15
<211> LENGTH: 339
<212> TYPE: DNA
<213> ORGANISM: Artificial Sequence
<220> FEATURE:
<223> OTHER INFORMATION: 2E8 Humanised VH Variant 5 Synthetic DNA

<400> SEQUENCE: 15
gaggtgcacc tggtggaatc cggcggagga ctggtgcagc ctggcggctc cctgagactg      60
tcttgcgccg cctccggctt caccttctcc agatacggca tgtcctgggt ccgacaggcc     120
cctggcaagg gactggaatg ggtggccatg atgaagacca agggcggcag aacctactac     180
cccgactccg tgaagggccg gttcaccatc tcccgggaca cgccaagaa ctccctgtac      240
```

```
ctgcagatga actccctgcg ggccgaggac accgccatct actactgcgc ctccgacggc    300
tactactggg gccagggcac caccgtgacc gtgtcatca                            339
```

<210> SEQ ID NO 16
<211> LENGTH: 333
<212> TYPE: DNA
<213> ORGANISM: Artificial Sequence
<220> FEATURE:
<223> OTHER INFORMATION: 2E8 Humanised VK Variant 1 Synthetic DNA

<400> SEQUENCE: 16

```
gacgtgctga tgacccagac cccccctgacc ctgtccgtga ccctgggcca gcctgcctcc    60
atctcctgca agtcctccca gtccctgctg cactccgacg gcaagaccta cctgaactgg   120
ctgcagcagc ggcctggcca gtcccccaag cggctgatct acctggtgtc caagctggac   180
tccggcgtgc ccgacagatt caccggctct ggctccggca ccgacttcac cctgaagatc   240
tcccgggtgg aagccgagga cgtgggcatc tactactgct ggcagggcac ccatctgtgg   300
accttcggcg gaggcacaaa ggtggaaatc aaa                                 333
```

<210> SEQ ID NO 17
<211> LENGTH: 333
<212> TYPE: DNA
<213> ORGANISM: Artificial Sequence
<220> FEATURE:
<223> OTHER INFORMATION: 2E8 Humanised VK Variant 2 Synthetic DNA

<400> SEQUENCE: 17

```
gacgtgctga tgacccagac cccccctgacc ctgtccgtga ccctgggcca gcctgcctcc    60
atctcctgca agtcctccca gtccctgctg cactccgacg gcaagaccta cctgaactgg   120
ctgcagcagc ggcctggcca gtctcctcgg cggctgatct acctggtgtc caagctggac   180
tccggcgtgc ccgacagatt caccggctct ggctccggca ccgacttcac cctgaagatc   240
tcccgggtgg aagccgagga cgtgggcatc tactactgct ggcagggcac ccatctgtgg   300
accttcggcg gaggcacaaa ggtggaaatc aaa                                 333
```

<210> SEQ ID NO 18
<211> LENGTH: 333
<212> TYPE: DNA
<213> ORGANISM: Artificial Sequence
<220> FEATURE:
<223> OTHER INFORMATION: 2E8 Humanised VK Variant 3 Synthetic DNA

<400> SEQUENCE: 18

```
gacgtgctga tgacccagac ccccctgtcc ctgtccgtga ccctgggcca gcctgcctcc    60
atctcctgca agtcctccca gtccctgctg cactccgacg gcaagaccta cctgaactgg   120
ctgcagcagc ggcctggcca gtctcctcgg cggctgatct acctggtgtc caagctggac   180
tccggcgtgc ccgacagatt caccggctct ggctccggca ccgacttcac cctgaagatc   240
tcccgggtgg aagccgagga cgtgggcatc tactactgct ggcagggcac ccatctgtgg   300
accttcggcg gaggcacaaa ggtggaaatc aaa                                 333
```

<210> SEQ ID NO 19
<211> LENGTH: 333
<212> TYPE: DNA
<213> ORGANISM: Artificial Sequence
<220> FEATURE:
<223> OTHER INFORMATION: 2E8 Humanised VK Variant 4 Synthetic DNA

<400> SEQUENCE: 19

```
gacgtggtga tgacccagac cccctgtcc ctgtccgtga ccctgggcca gcctgcctcc    60
atctcctgca agtcctccca gtccctgctg cactccgacg gcaagaccta cctgaactgg   120
ctgcagcagc ggcctggcca gtctcctcgg cggctgatct acctggtgtc caagctggac   180
tccggcgtgc ccgacagatt ctccggctct ggctccggca ccgacttcac cctgaagatc   240
tcccgggtgg aagccgagga cgtgggcatc tactactgct ggcagggcac ccatctgtgg   300
accttcggcg gaggcacaaa ggtggaaatc aaa                                333
```

<210> SEQ ID NO 20
<211> LENGTH: 113
<212> TYPE: PRT
<213> ORGANISM: Artificial Sequence
<220> FEATURE:
<223> OTHER INFORMATION: 2E8 Humanised VH Variant 1 Peptide

<400> SEQUENCE: 20

```
Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Leu Val
        35                  40                  45

Ala Met Met Lys Thr Lys Gly Gly Arg Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Lys Ala Glu Asp Thr Ala Ile Tyr Phe Cys
                85                  90                  95

Ala Ser Asp Gly Tyr Tyr Trp Gly Gln Gly Thr Thr Val Thr Val Ser
            100                 105                 110

Ser
```

<210> SEQ ID NO 21
<211> LENGTH: 113
<212> TYPE: PRT
<213> ORGANISM: Artificial Sequence
<220> FEATURE:
<223> OTHER INFORMATION: 2E8 Humanised VH Variant 2 Peptide

<400> SEQUENCE: 21

```
Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Leu Val
        35                  40                  45

Ala Met Met Lys Thr Lys Gly Gly Arg Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Phe Cys
                85                  90                  95

Ala Ser Asp Gly Tyr Tyr Trp Gly Gln Gly Thr Thr Val Thr Val Ser
            100                 105                 110

Ser
```

```
<210> SEQ ID NO 22
<211> LENGTH: 113
<212> TYPE: PRT
<213> ORGANISM: Artificial Sequence
<220> FEATURE:
<223> OTHER INFORMATION: 2E8 Humanised VH Variant 3 Peptide

<400> SEQUENCE: 22
```

Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Leu Val
        35                  40                  45

Ala Met Met Lys Thr Lys Gly Gly Arg Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Ser Asp Gly Tyr Tyr Trp Gly Gln Gly Thr Thr Val Thr Val Ser
            100                 105                 110

Ser

```
<210> SEQ ID NO 23
<211> LENGTH: 113
<212> TYPE: PRT
<213> ORGANISM: Artificial Sequence
<220> FEATURE:
<223> OTHER INFORMATION: 2E8 Humanised VH Variant 4 Peptide

<400> SEQUENCE: 23
```

Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Leu Val
        35                  40                  45

Ala Met Met Lys Thr Lys Gly Gly Arg Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Asp Gly Tyr Tyr Trp Gly Gln Gly Thr Thr Val Thr Val Ser
            100                 105                 110

Ser

```
<210> SEQ ID NO 24
<211> LENGTH: 113
<212> TYPE: PRT
<213> ORGANISM: Artificial Sequence
<220> FEATURE:
<223> OTHER INFORMATION: 2E8 Humanised VH Variant 5 Peptide

<400> SEQUENCE: 24
```

Glu Val His Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ala Met Met Lys Thr Lys Gly Gly Arg Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Ser Asp Gly Tyr Tyr Trp Gly Gln Gly Thr Thr Val Thr Val Ser
            100                 105                 110

Ser

<210> SEQ ID NO 25
<211> LENGTH: 111
<212> TYPE: PRT
<213> ORGANISM: Artificial Sequence
<220> FEATURE:
<223> OTHER INFORMATION: 2E8 Humanised VK Variant 1 Peptide

<400> SEQUENCE: 25

Asp Val Leu Met Thr Gln Thr Pro Leu Thr Leu Ser Val Thr Leu Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Ile Tyr Tyr Cys Trp Gln Gly
                85                  90                  95

Thr His Leu Trp Thr Phe Gly Gly Gly Thr Lys Val Glu Ile Lys
            100                 105                 110

<210> SEQ ID NO 26
<211> LENGTH: 111
<212> TYPE: PRT
<213> ORGANISM: Artificial Sequence
<220> FEATURE:
<223> OTHER INFORMATION: 2E8 Humanised VK Variant 2 Peptide

<400> SEQUENCE: 26

Asp Val Leu Met Thr Gln Thr Pro Leu Thr Leu Ser Val Thr Leu Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Ile Tyr Tyr Cys Trp Gln Gly
                85                  90                  95
```

```
<210> SEQ ID NO 27
<211> LENGTH: 111
<212> TYPE: PRT
<213> ORGANISM: Artificial Sequence
<220> FEATURE:
<223> OTHER INFORMATION: 2E8 Humanised VK Variant 3 Peptide

<400> SEQUENCE: 27

Asp Val Leu Met Thr Gln Thr Pro Leu Ser Leu Ser Val Thr Leu Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Ile Tyr Tyr Cys Trp Gln Gly
                85                  90                  95

Thr His Leu Trp Thr Phe Gly Gly Gly Thr Lys Val Glu Ile Lys
            100                 105                 110

<210> SEQ ID NO 28
<211> LENGTH: 111
<212> TYPE: PRT
<213> ORGANISM: Artificial Sequence
<220> FEATURE:
<223> OTHER INFORMATION: 2E8 Humanised VK Variant 4 Peptide

<400> SEQUENCE: 28

Asp Val Val Met Thr Gln Thr Pro Leu Ser Leu Ser Val Thr Leu Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Trp Gln Gly
                85                  90                  95

Thr His Leu Trp Thr Phe Gly Gly Gly Thr Lys Val Glu Ile Lys
            100                 105                 110
```